(12) United States Patent
Nakamura

(10) Patent No.: US 11,160,889 B2
(45) Date of Patent: Nov. 2, 2021

(54) ULTRAVIOLET IRRADIATION DEVICE FOR STERILIZING FLUID FLOW

(71) Applicant: Enplas Corporation, Saitama (JP)

(72) Inventor: Masato Nakamura, Saitama (JP)

(73) Assignee: Enplas Corporation, Saitama (JP)

(*) Notice: Subject to any disclaimer, the term of this patent is extended or adjusted under 35 U.S.C. 154(b) by 0 days.

(21) Appl. No.: 16/649,653

(22) PCT Filed: Jul. 25, 2018

(86) PCT No.: PCT/JP2018/027832
§ 371 (c)(1),
(2) Date: Mar. 22, 2020

(87) PCT Pub. No.: WO2019/064864
PCT Pub. Date: Apr. 4, 2019

(65) Prior Publication Data
US 2020/0268918 A1    Aug. 27, 2020

(30) Foreign Application Priority Data
Sep. 28, 2017 (JP) .............................. JP2017-188148

(51) Int. Cl.
*A61L 2/10* (2006.01)
*A61L 2/26* (2006.01)
*C02F 1/32* (2006.01)

(52) U.S. Cl.
CPC .................. *A61L 2/10* (2013.01); *A61L 2/26* (2013.01); *C02F 1/325* (2013.01);
(Continued)

(58) Field of Classification Search
CPC .......... A61L 2/10; A61L 2/26; A61L 2202/11; A61L 2202/122; A61L 9/20;
(Continued)

(56) References Cited

U.S. PATENT DOCUMENTS 5,635,133 A    6/1997  Glazman
9,321,658 B2 *  4/2016  Chen ....................... C02F 1/325
(Continued)

FOREIGN PATENT DOCUMENTS

JP          84565      9/1929
JP       11-512000    10/1999
(Continued)

OTHER PUBLICATIONS

International Search Report and the Written Opinion dated Sep. 4, 2018 From the International Searching Authority Re. Application No. PCT/JP2018/027832 and Its Translation of Search Report Into English. (9 Pages).

*Primary Examiner* — Brooke Purinton

(57) ABSTRACT

The purpose of the present invention is to provide an ultraviolet sterilization device that can increase the ultraviolet irradiance near the center of a treatment flow path even at a position far from a light emitting element. This ultraviolet sterilization device comprises: a flow path tube having a linear treatment flow path therein; a light emitting element for emitting ultraviolet rays; and a reflector having a reflection surface for reflecting ultraviolet rays emitted from the light emitting element and collecting and directing the ultraviolet rays to the flow path tube. The ultraviolet sterilization device irradiates a fluid flowing in the linear treatment flow path with ultraviolet rays and sterilizes the fluid.

9 Claims, 13 Drawing Sheets

(52) U.S. Cl.
CPC ...... *A61L 2202/11* (2013.01); *A61L 2202/122* (2013.01); *C02F 2201/3228* (2013.01)

(58) Field of Classification Search
CPC ............... A61L 2202/123; C02F 1/325; C02F 2201/3228; C02F 2201/3222; G02B 5/10; G02B 17/00
See application file for complete search history.

(56) References Cited

U.S. PATENT DOCUMENTS

| | | | | |
|---|---|---|---|---|
| 2010/0178201 | A1* | 7/2010 | Tribelsky | A61L 9/205 422/24 |
| 2015/0129776 | A1* | 5/2015 | Boodaghians | C02F 1/325 250/432 R |
| 2015/0129777 | A1 | 5/2015 | Nikamoto | |
| 2015/0314024 | A1* | 11/2015 | Khan | C02F 1/325 250/435 |
| 2018/0257953 | A1 | 9/2018 | Mochizuki et al. | |

FOREIGN PATENT DOCUMENTS

| | | |
|---|---|---|
| JP | 2017-104230 | 6/2017 |
| WO | WO 2013/175931 | 11/2013 |
| WO | WO 2017/056902 | 4/2017 |
| WO | WO 2019/064864 | 4/2019 |

\* cited by examiner

ULTRAVIOLET IRRADIATION DEVICE FOR STERILIZING FLUID FLOW

TECHNICAL FIELD

The present invention relates to an ultraviolet sterilization apparatus and an ultraviolet irradiation apparatus.

BACKGROUND ART

It is well known that fluids such as liquids can be sterilized with ultraviolet radiation. For example, Patent Literature (hereinafter, referred to as "PTL") 1 describes a fluid sterilization apparatus that directs ultraviolet radiation in the axial direction of a channel onto the channel extending in the axial direction, so as to sterilizes a liquid flowing through the channel.

Specifically, the fluid sterilization apparatus described in PTL 1 includes a channel pipe that demarcates a treatment channel extending in the axial direction, and a wide-orientation-angle light emitting element (LED light source) that is disposed in the vicinity of one end portion of the channel pipe and emits ultraviolet radiation in the axial direction from the one end toward the treatment channel. The ultraviolet radiation emitted from the light source at a wide angle propagates in the longitudinal (axial) direction of the treatment channel while being reflected on the inner surface of the treatment channel to sterilize a fluid inside the treatment channel.

It is preferred in PTL 1 that the wide-orientation-angle light emitting element with a beam angle of full width at half maximum of about 120 degrees be disposed such that the ultraviolet radiation in the range of the beam angle of full width at half maximum entirely enters the treatment channel.

CITATION LIST

Patent Literature

PTL 1
Japanese Patent Application Laid-Open No. 2017-104230

SUMMARY OF INVENTION

Technical Problem

To effectively sterilize the fluid flowing through the channel pipe, it is desirable to treat the flowing fluid at as high an illuminance as possible and/or for as long a time as possible.

Generally, in a case where the wide-orientation-angle light emitting element is used in the same way as the fluid sterilization apparatus described in PTL 1, although when light exits the light emitting element, the exiting light has a high illuminance in the vicinity of the light emitting surface at its portion forming an orthogonal or nearly orthogonal angle with the light emitting surface (at a central portion of a light flux), the illuminance decreases as the angle formed by the exiting light with the light emitting surface becomes parallel to the light emitting surface. For this reason, the illuminance near the center of the treatment channel seems to increase when the aforementioned central portion of the light flux is brought into substantial alignment with a portion of the treatment channel near its center. However, the flux of the light emitted from the wide-orientation-angle light emitting element spreads with increasing distance from the light emitting surface. Accordingly, it is likely that the illuminance distribution becomes uniform and the illuminance decreases with increasing distance from the light source. Therefore, in the fluid sterilization apparatus described in PTL 1, although it is possible to obtain a high illuminance at the center of the treatment channel in the vicinity of the light emitting element, it is difficult at a distance from the light emitting element to increase the illuminance at the center of the treatment channel. Consequently, it is difficult to treat the fluid at a high illuminance or for a long time over the entire treatment channel, and thus to enhance the sterilization effect sufficiently.

Accordingly, the present invention is intended to provide an ultraviolet sterilization apparatus that sterilizes a fluid flowing through the inside of a treatment channel by irradiation of the fluid with ultraviolet radiation from a light emitting element and an ultraviolet irradiation apparatus, which are capable of enhancing the sterilization effect over the entire treatment channel.

Solution to Problem

An ultraviolet sterilization apparatus in relation to the present invention for solving the above-described technical problem is an ultraviolet sterilization apparatus that sterilizes a fluid flowing through a linear treatment channel by irradiation of the fluid with ultraviolet radiation, the ultraviolet sterilization apparatus, including: a channel pipe having therein the linear treatment channel; a light emitting element that emits the ultraviolet radiation; and a reflector having a reflective surface that reflects the ultraviolet radiation emitted from the light emitting element to collect the ultraviolet radiation toward the channel pipe.

In addition, an ultraviolet irradiation apparatus in relation to the present invention for solving the above-described technical problem is an ultraviolet irradiation apparatus for sterilizing a fluid flowing through a linear treatment channel by irradiation of the fluid with ultraviolet radiation, the ultraviolet irradiation apparatus, including: a light emitting element that emits the ultraviolet radiation; and a reflector having a reflective surface that reflects the ultraviolet radiation emitted from the light emitting element to collect the ultraviolet radiation in a direction in which a channel pipe is to be disposed.

Advantageous Effects of Invention

According to the present invention, an ultraviolet sterilization apparatus and an ultraviolet irradiation apparatus are provided which are capable of enhancing the sterilization effect over the entire treatment channel.

DESCRIPTION OF EMBODIMENT

An embodiment of the present invention is described below in detail with reference to the accompanying drawings.

[Configuration of Ultraviolet Sterilization Apparatus]

Figure 1:
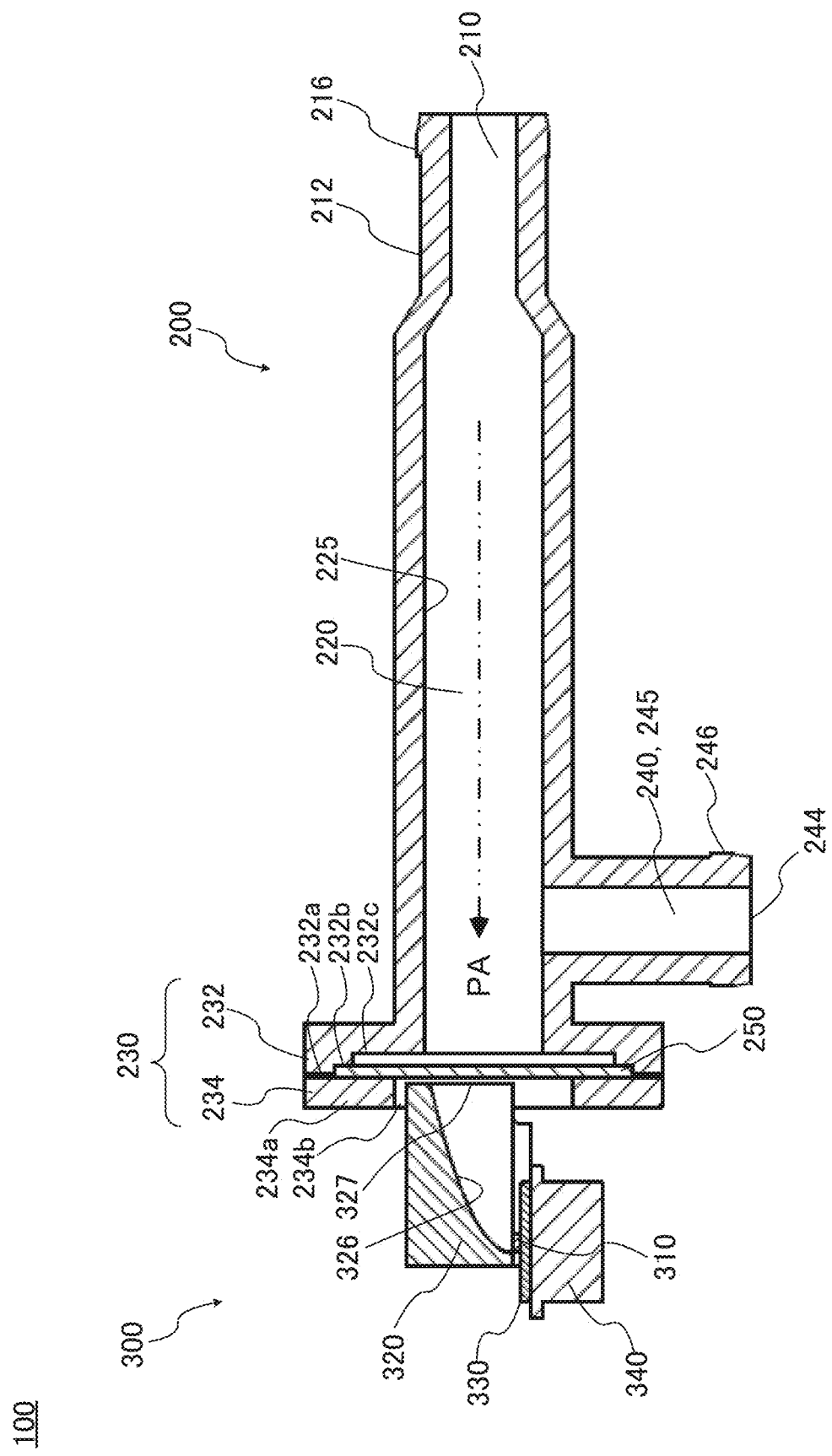
FIG. 1 is a sectional view of an ultraviolet sterilization apparatus according to an embodiment of the present invention, taken along the vertical direction and a direction extending along a fluid flowing direction of a channel pipe.

FIG. 1 is a sectional view of ultraviolet sterilization apparatus 100 including channel pipe 200 and ultraviolet irradiation apparatus 300 according to the present embodiment, taken along the vertical direction and the direction extending along the fluid flowing direction of channel pipe 200. Note that "fluid" is used herein in the sense that it encompasses substances such as liquids, gases, and the like that can flow through the treatment channel.

Channel pipe 200 has therein linear treatment channel 220 through which a fluid to be treated flows from one end side to the other end side. Transparent plate 250 capable of transmitting ultraviolet radiation is disposed on end portion 230 of channel pipe 200 which forms the end of treatment channel 220, while making contact with treatment channel 220.

Ultraviolet irradiation apparatus 300 includes light emitting element 310 that emits ultraviolet radiation and reflector 320 that collects the ultraviolet radiation emitted from light emitting element 310 and causes the ultraviolet radiation to exit in one direction. Ultraviolet irradiation apparatus 300 is disposed outside of treatment channel 220 facing end portion 230 of channel pipe 200 and directs, in the linear direction of linear treatment channel 220 and in a direction opposite to the direction in which the fluid flows through treatment channel 220, the ultraviolet radiation collected by reflector 320 via transparent plate 250 onto the fluid flowing through treatment channel 220.

(Channel Pipe)

Channel pipe 200 is a linear pipe having channel wall 225 whose inner surface is formed substantially cylindrically. Channel pipe 200 has inflow port 210, channel wall 225 defining the outer circumference of treatment channel 220, end portion 230, and outflow port 240, which are integrally molded. Inflow port 210, treatment channel 220, and outflow port 240 are configured to communicate with one another in this order, and allow fluids to flow therethrough.

Inflow port 210 is an opening portion formed in one end side of channel pipe 200 for introducing a fluid to be sterilized with ultraviolet irradiation into treatment channel 220, and is configured to be coupled with an external fluid supply apparatus to allow the fluid from the fluid supply apparatus to flow through treatment channel 220. For example, inflow port 210 may include fit-in portion 212 that is narrowed such that a hose from the fluid supply apparatus can be fit thereto as illustrated in FIG. 1. Fit-in portion 212 may also have inflow engagement portion 216 that has a detent shape protruding toward the downstream side of treatment channel 220 and that does not much inhibit insertion of the hose but is engaged with the hose to prevent the hose from being freely pulled out.

Treatment channel 220 is a linear channel through which the fluid to be treated flows, and also is a substantially cylindrical channel having a shape that is rotationally symmetrical to axis PA formed in the linear direction of linear treatment channel 220. Treatment channel 220 only have to be of such a size as to allow adequate sterilization of the fluid by irradiation with ultraviolet radiation. For example, when the optical output per one light emitting element is 30 mW, treatment channel 220 may have an inner diameter of 5 cm or less, and a channel length of 2 cm or more and 30 cm or less. Note that "axis PA" of the treatment channel as used herein means a virtual straight line connecting centers of treatment channel 220 in sections perpendicular to the flowing direction of the fluid through treatment channel 220.

Channel wall 225 is an inner wall surface of channel pipe 200, and the inner surface of channel wall 225 is formed in a substantially cylindrical shape to define the outer circumference of the treatment channel 220.

End portion 230 is an end portion situated opposite inflow port 210 of treatment channel 220. End portion 230 includes transparent-plate holding portion 232 having an outer diameter that is greater than the inner diameter of treatment channel 220 and the outer diameter of transparent plate 250, and transparent-plate fixation lid 234 joined to transparent-plate holding portion 232 to fix transparent plate 250.

Outflow port 240 is an opening portion formed on the other end side of channel pipe 200 in the vicinity of end portion 230, from which a fluid flowing through treatment channel 220 is discharged. Outflow port 240 is configured to allow the fluid in treatment channel 220 to flow to the outside. Outflow port 240 is formed in such a position that the flowing direction of the fluid flowing through treatment channel 220 and the flowing direction of the fluid discharged from outflow port 240 are not on the same line. For example, outflow port 240 may be formed in the vicinity of end portion 230 in a direction substantially orthogonal to treatment channel 220. In this case, as illustrated in FIG. 1, opening 244 of outflow port 240 may be disposed in a position distant from the perimeter of treatment channel 220, and outflow channel 245 communicating from treatment channel 220 to opening 244 may be disposed. Outflow port 240 may have a shape allowing a hose for guiding the fluid to a fluid reservoir or the like to be fit to outflow port 240. Outflow port 240 may also have outflow engagement portion 246 that has a detent shape protruding toward the upstream side of treatment channel 220 and that does not much inhibit insertion of the hose but is engaged with the hose to prevent the hose from being freely pulled out.

Transparent plate 250 is a UV-transmissive member that is held at end portion 230 and serves as a window for guiding ultraviolet radiation emitted from ultraviolet irradiation apparatus 300 into the inside of treatment channel 220. Transparent plate 250 also forms part of the outer circumference of the treatment channel to prevent the fluid from leaking from end portion 230 in the flowing direction.

Figure 2:
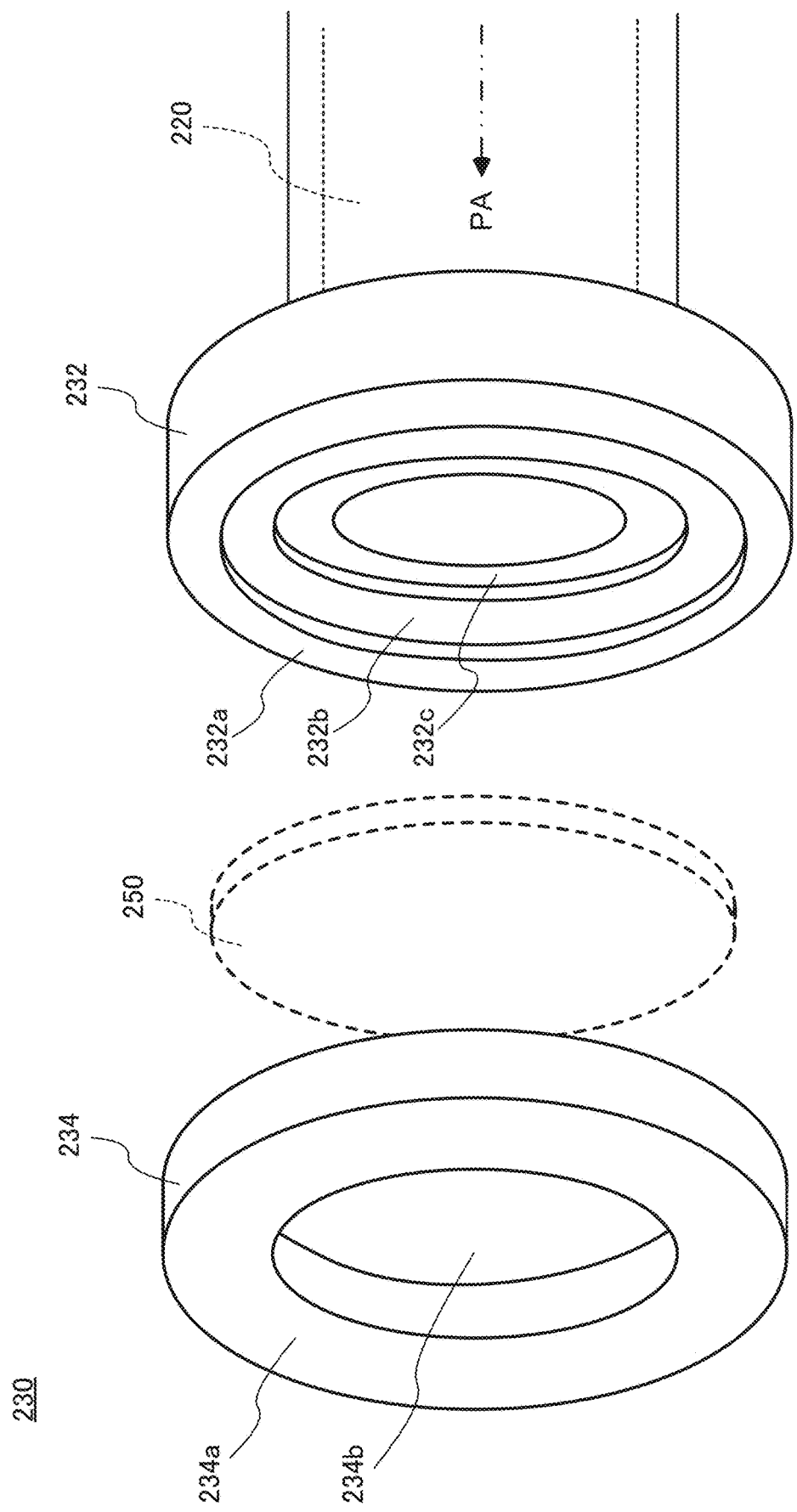
FIG. 2 is a schematic front exploded perspective view of an end portion of the channel pipe in which a transparent-plate holding portion and a transparent-plate fixation lid are separated.

FIG. 2 is a schematic front exploded perspective view of end portion 230 in which transparent-plate holding portion 232 and transparent-plate fixation lid 234 are separated. Note that, for ease of understanding, transparent plate 250 (dashed line) is also illustrated in FIG. 2. Note also that, transparent-plate holding portion 232 and transparent-plate fixation lid 234 may have tapped holes or the like for insertion of screws for joining of transparent-plate holding portion 232 and transparent-plate fixation lid 234, and transparent-plate fixation lid 234 may have tapped holes or the like for joining to reflector 320, although illustration of those tapped holes is omitted in FIG. 2 and in the description below.

Transparent-plate holding portion 232 includes end-portion outer wall portion 232a, transparent-plate disposing portion 232b, which is a cylindrical fitting portion in which UV-transmissive transparent plate 250 is fittingly disposed, and flow-rate attenuation portion 232c, which is a cylindrical fitting portion serving as a region where transparent plate 250 makes contact with fluids. End-portion outer wall portion 232a, transparent-plate disposing portion 232b, and flow-rate attenuation portion 232c are formed in this order from outside to inside.

End-portion outer wall portion 232a is a cylindrical member having an outer diameter greater than the inner diameter of treatment channel 220 and the outer diameter of transparent plate 250. Further, circular transparent-plate disposing portion 232b is fittingly formed inside of end-portion outer wall portion 232a. Thus, the shape of end-portion outer wall portion 232a is such that the surface of end-portion outer wall portion 232a facing transparent-plate fixation lid 234 is sandwiched between two concentric circles. End-portion outer wall portion 232a only have to have a size and strength large and high enough to fix transparent plate 250. End-portion outer wall portion 232a may also have tapped holes (not illustrated) for joining to fixation outer wall portion 234a of transparent-plate fixation lid 234.

Transparent-plate disposing portion 232b is a cylindrical fitting portion being formed inside of end-portion outer wall portion 232a and having an outer diameter substantially the same as the outer diameter of transparent plate 250. Further, cylindrical flow-rate attenuation portion 232c is fittingly formed inside of transparent-plate disposing portion 232b. Thus, transparent-plate disposing portion 232b is a fitting portion having a certain depth and shaped such that the bottom surface of transparent-plate disposing portion 232b is sandwiched between two concentric circles. Transparent-plate disposing portion 232b has an outer diameter smaller than the outer diameter of end-portion outer wall portion 232a and greater than the outer diameter of flow-rate attenuation portion 232c, and holds transparent plate 250 at a step portion that is a bottom surface formed by transparent-plate disposing portion 232b and flow-rate attenuation portion 232c. The depth of transparent-plate disposing portion 232b only have to be substantially the same as the thickness of transparent plate 250. The width between the aforementioned two concentric circles only have to be large enough to hold transparent plate 250.

Flow-rate attenuation portion 232c is a cylindrical fitting portion formed inside of transparent-plate disposing portion 232b. Further, treatment channel 220 is opened inside of flow-rate attenuation portion 232c. Thus, flow-rate attenuation portion 232c is a fitting portion having a certain depth and shaped such that the bottom surface of flow-rate attenuation portion 232c is sandwiched between two concentric circles. Flow-rate attenuation portion 232c has an outer diameter smaller than the outer diameter of transparent-plate disposing portion 232b and transparent plate 250 and greater than the outer diameter of treatment channel 220, and forms a space for attenuating (reducing) the flow rate of the fluid flowing through the treatment channel so as to prevent transparent plate 250 from being broken and damaged due to impact of the fluid flowing through treatment channel 220 on transparent plate 250. The depth of flow-rate attenuation portion 232c only have to be deep enough to allow the fluid flowing through treatment channel 220 to spread into flow-rate attenuation portion 232c. The size of flow-rate attenuation portion 232c only have to be large enough to hold transparent plate 250 at the aforementioned step portion.

Transparent-plate fixation lid 234 joins to end-portion outer wall portion 232a of transparent-plate holding portion 232 and fixes transparent plate 250 disposed in transparent-plate disposing portion 232b from the outside (the side opposite to treatment channel 220). Transparent-plate fixation lid 234 has fixation outer wall portion 234a and ultraviolet irradiation hole 234b, which is a through hole formed inside fixation outer wall portion 234a.

Fixation outer wall portion 234a can be joined to end-portion outer wall portion 232a, and when joined to end-portion outer wall portion 232a, makes contact also with transparent plate 250 to position transparent plate 250. Fixation outer wall portion 234a only have to have a size and strength large and high enough to be joined to end outer wall 232a for fixation of transparent plate 250. Fixation outer wall portion 234a may have tapped holes (not illustrated) for joining to reflector 320 of ultraviolet irradiation apparatus 300.

Ultraviolet irradiation hole 234b is a through hole having an outer diameter smaller than the outer diameter of transparent plate 250 and greater than the outer diameter of treatment channel 220 and formed in fixation outer wall portion 234a. The outer diameter of ultraviolet irradiation hole 234b may be larger or smaller than the outer diameter of flow-rate attenuation portion 232c. Ultraviolet irradiation hole 234b transmits ultraviolet radiation exiting reflector 320 of ultraviolet irradiation apparatus 300. The transmitted ultraviolet radiation is guided via transparent plate 250 to treatment channel 220. From the viewpoint of reducing the loss of the amount of light of ultraviolet radiation exiting reflector 320 and propagating through the air by bringing reflector 320 and transparent plate 250 closer to each other, it is preferable that ultraviolet irradiation hole 234b be shaped to be capable of accommodating within the inside of the through hole the outer circumference of reflector 320 on the ultraviolet-radiation exit side.

The fluid introduced from inflow port 210 into treatment channel 220 is irradiated with ultraviolet radiation from ultraviolet irradiation apparatus 300 via transparent plate 250, so as to be sterilized during flowing through treatment channel 220 between inflow port 210 and end portion 230. Then, the sterilized fluid is discharged from outflow port 240. Note that the fluid is partially discharged from outflow port 240 after irradiated with ultraviolet radiation in treatment channel 220 and sterilized, without flowing toward end portion 230. It is possible to sufficiently sterilize the fluid by irradiation with ultraviolet irradiation during a period when the fluid is flowing through treatment channel 220, whichever stream the fluid flows through.

The fluid may be a substance that is to be sterilized and is capable of flowing through the treatment channel, and may, for example, be water or the like in the case of a liquid. The fluid may also be service water including drinking water, agricultural water, and the like, or sewage including wastewater from factories and the like.

The flow rate of the fluid may be any flow rate as long as the fluid is sufficiently sterilized by irradiation with ultraviolet radiation when the fluid is flowing through treatment channel 220, and may, for example, be 10 l/min or less in a case where the optical output per one light emitting element is 30 mW and the fluid is a liquid.

Channel pipe 200 is formed of a material which is resistant to deformation or breakage due to the pressure of the flowing fluid, and is formed, for example, of a metallic material, a resinous material, or the like. The inner surfaces of channel wall 225 and end portion 230 (particularly flow-rate attenuation portion 232c), both of which define the outer circumference of treatment channel 220, may be formed of a material with high UV reflectivity or a material with low UV reflectivity.

In a case where the inner surfaces are formed of a material with high UV reflectivity, the inner surfaces of channel wall 225 and end portion 230 are preferably formed of mirror-polished aluminum (Al), polytetrafluoroethylene (PTFE), or the like, and are more preferably formed of PTFE that is chemically stable and has high UV reflectivity, for example. Of the ultraviolet radiation introduced from ultraviolet irradiation apparatus 300 into treatment channel 220, a light beam propagating while slightly spreading can be reflected on the inner surfaces of channel wall 225 and end portion 230 when these inner surfaces are formed of a material with high UV reflectivity.

In contrast, in a case where the inner surfaces are formed of a material with low UV reflectivity, it is possible, for example, to maintain the high sterilization efficiency by designing the shape of the reflector such that the light beam travels inside channel pipe 200 while reflected as little as possible on the inner surfaces. Such a design makes it possible to use an inexpensive material such as vinyl chloride or the like for the channel pipe, so as to reduce the cost of the apparatus.

Transparent plate 250 is formed of an UV transmissive material. For example, it is preferable that transparent plate 250 be formed of a material capable of transmitting ultraviolet radiation with a wavelength of 200 nm or higher and 350 nm or less, and it is more preferable that transparent plate 250 be formed of a material capable of transmitting ultraviolet radiation with a wavelength of 260 nm or higher and 290 nm or less with a higher sterilization efficiency. Examples of the material of transparent plate 250 include materials with high transmittance to ultraviolet radiation with the aforementioned wavelengths, such as quartz ($SiO_2$), sapphire ($Al_2O_3$), amorphous fluorinated resins, and the like.

(Ultraviolet Irradiation Apparatus)

Ultraviolet irradiation apparatus 300 includes light emitting element 310 mounted on substrate 330 and reflector 320 that collects ultraviolet radiation emitted from light emitting element 310.

Light emitting element 310 may be an element capable of emitting ultraviolet radiation, and may, for example, be a light emitting diode (LED) having a center wavelength or a peak wavelength of 200 nm or higher and 350 nm or less, or may preferably be an LED having a center wavelength or a peak wavelength of 260 nm or higher and 290 nm or less with a higher sterilization efficiency.

It is preferable that light emitting element 310 have a wide orientation angle, and for example, it is preferable that light emitting element 310 be an LED with a beam angle of full width at half maximum of 60 degrees or more, which is an angle between the directions where the brightness intensity is 50% of the peak value.

Light emitting element 310 is mounted on substrate 330 and substrate 330 is mounted on substrate mount 340.

Reflector 320 is a light collecting member having reflective surface 326 that reflects ultraviolet radiation emitted from light emitting element 310 to collect it, and exit aperture 327 from which the collected ultraviolet radiation exits.

Figure 3:
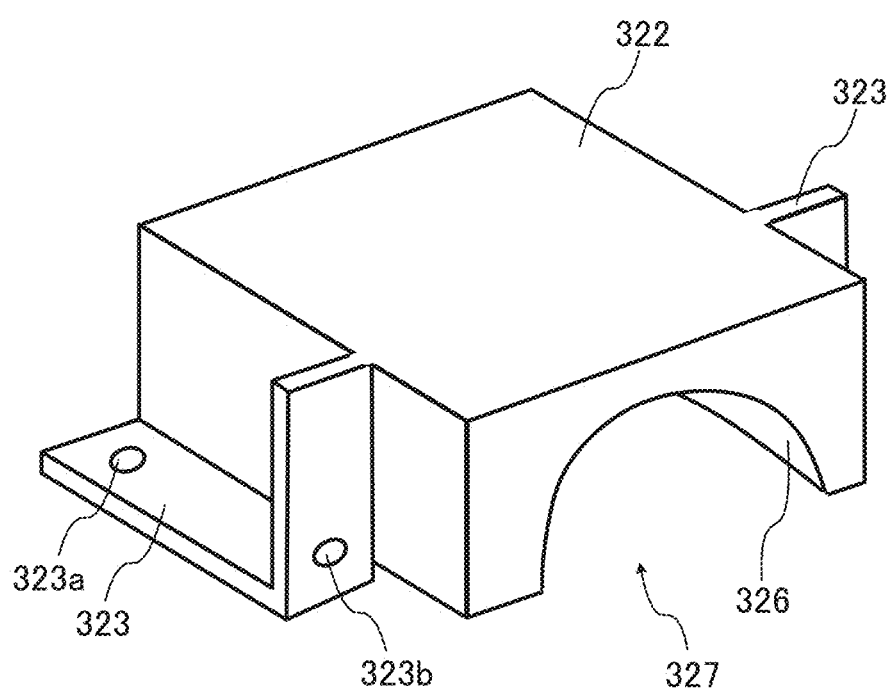
FIG. 3 is a schematic perspective view of a reflector.

FIG. 3 is a schematic perspective view of reflector 320. FIGS. 4A, 4B, 4C, 4D, 4E and 4F, and 5 illustrate the shape of a reflector which satisfies below-described conditions 1 and 2. FIGS. 6A, 6B, 6C, 6D, 6E and 6F, and 7 illustrate the shape of a reflector which satisfies below-described conditions 1 and 3.

Figure 4E:
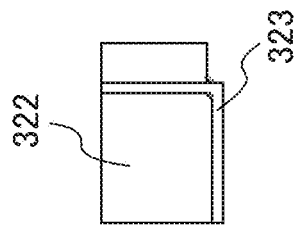
FIG. 4E is a side view of the reflector.
Figure 4F:
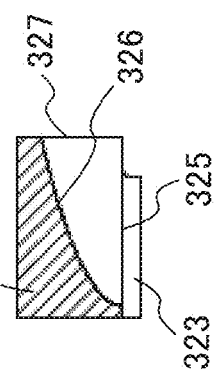
FIG. 4F is a sectional view of the reflector taken along line 4F-4F.
Figure 4C:
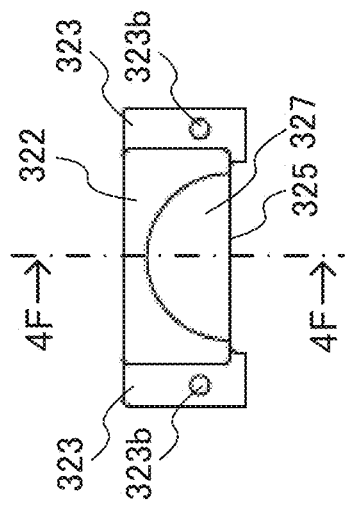
FIG. 4C is a front view of the reflector.
Figure 4D:
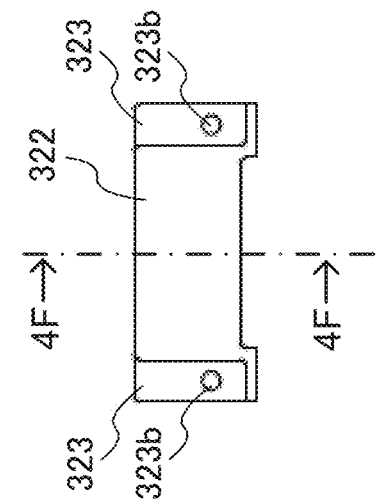
FIG. 4D is a rear view of the reflector.
Figure 4A:
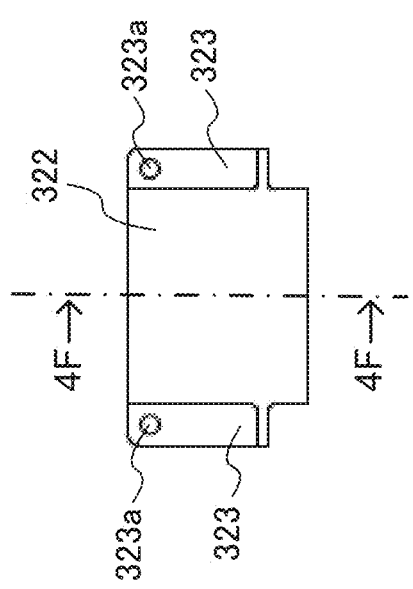
FIG. 4A is a plan view of the reflector.
Figure 4B:
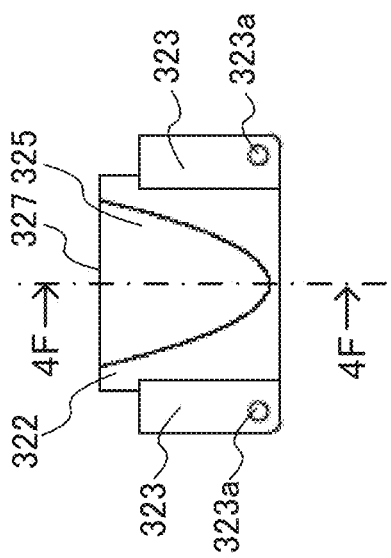
FIG. 4B is a bottom view of the reflector.
Figure 5:
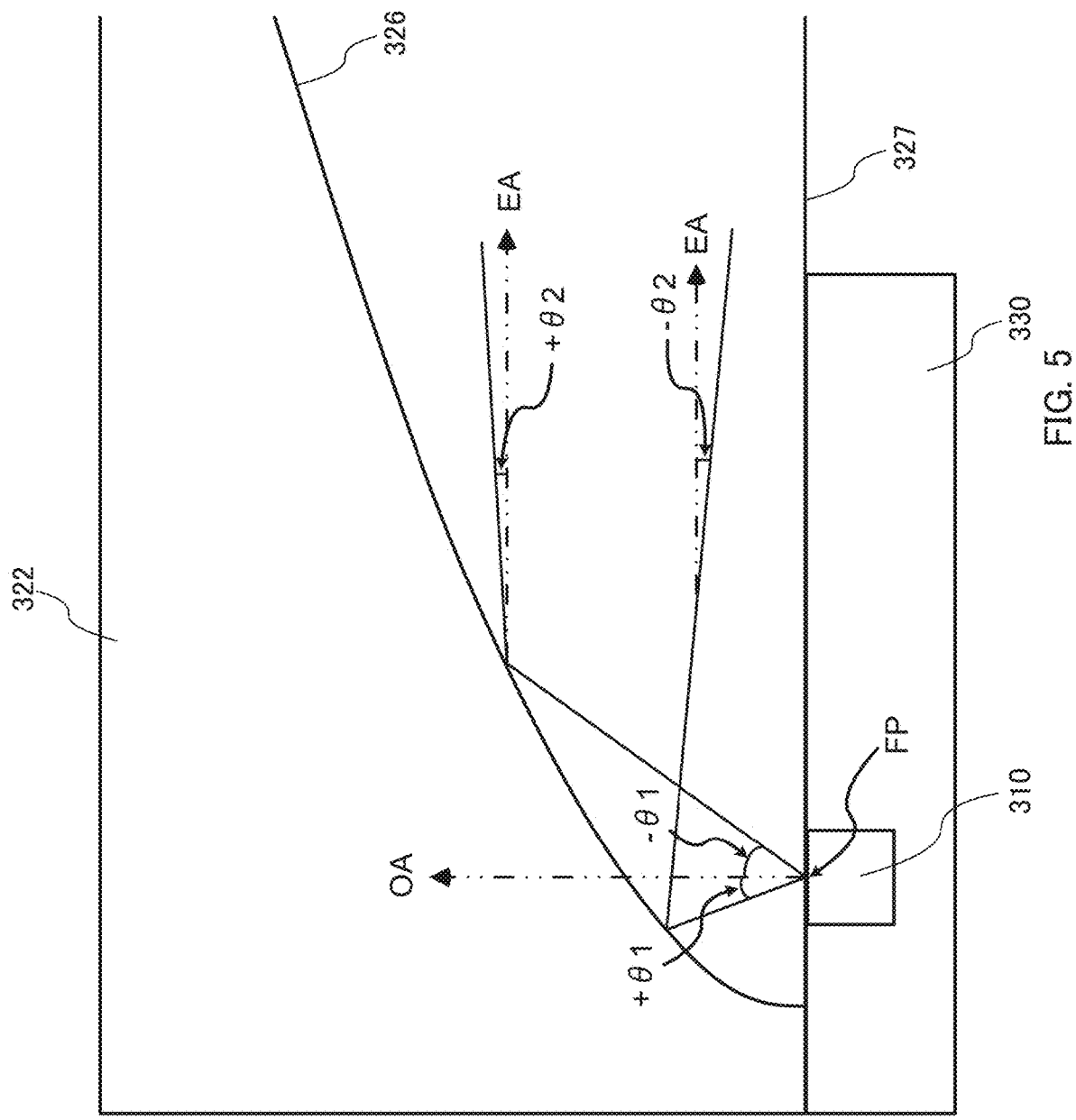
FIG. 5 is an optical-path diagram illustrating optical paths of typical light beams included in ultraviolet radiation emitted from a light emitting element.
Figure 6A:
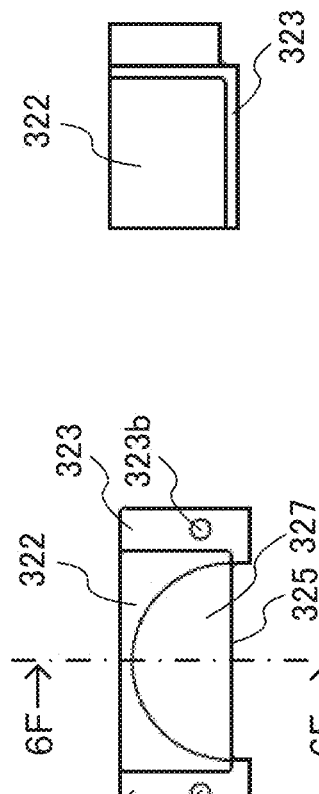
FIG. 6A is a plan view of the reflector.
Figure 6C:
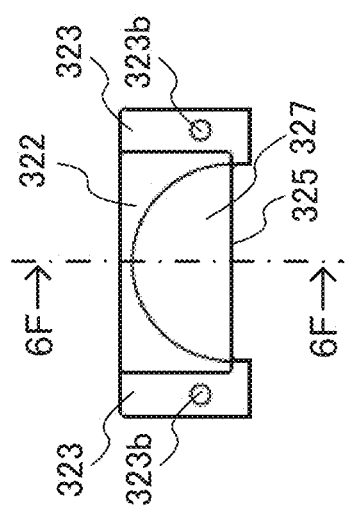
FIG. 6C is a front view of the reflector.
Figure 6E:
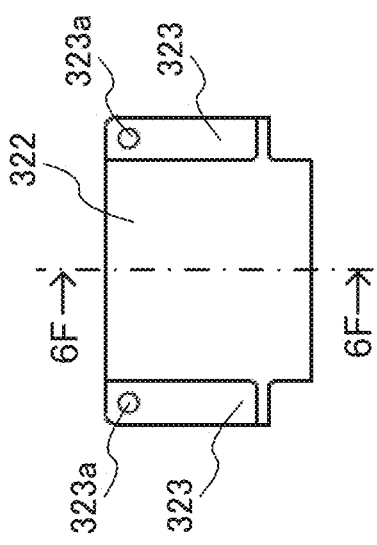
FIG. 6E is a side view of the reflector.
Figure 6B:
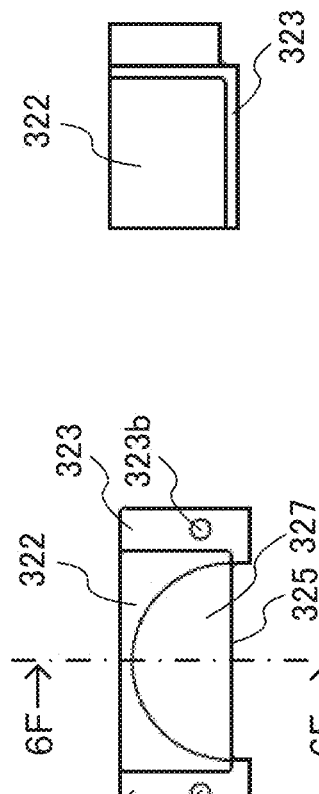
FIG. 6B is a bottom view of the reflector.
Figure 6D:
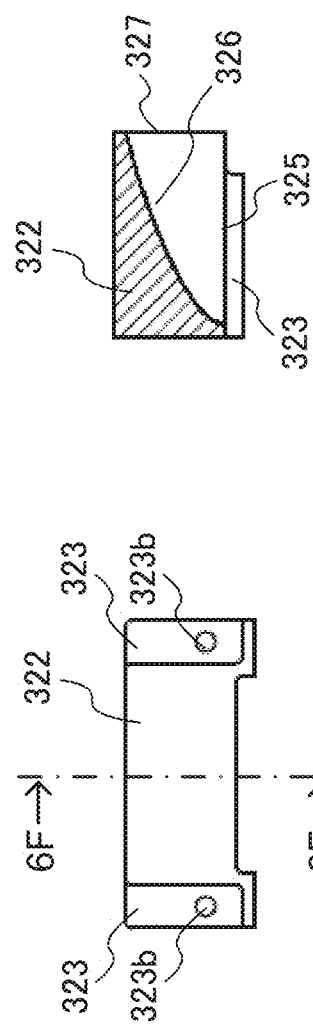
FIG. 6D is a rear view of the reflector.
Figure 6F:
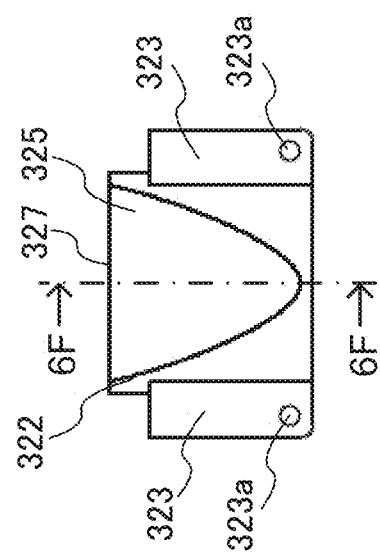
FIG. 6F is a sectional view of the reflector taken along line 6F-6F.
Figure 7:
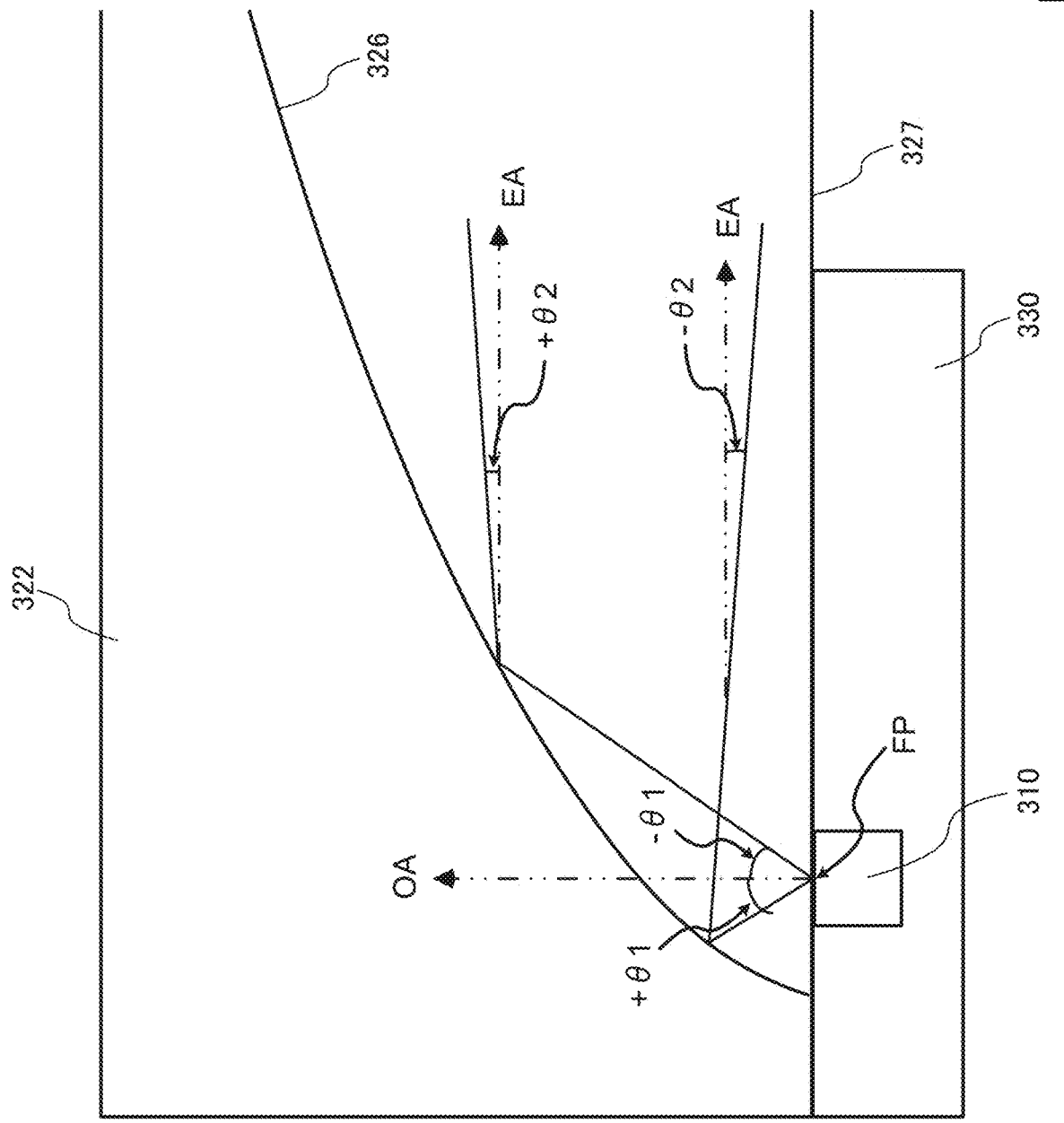
FIG. 7 is an optical-path diagram illustrating optical paths of typical light beams included in ultraviolet radiation emitted from the light emitting element.

FIGS. 4A and 6A are plan views of reflector 320, FIGS. 4B and 6B are bottom views of reflector 320, FIGS. 4C and 6C are front views of reflector 320, FIGS. 4D and 6D are rear views of reflector 320, FIGS. 4E and 6E are side views of reflector 320, and FIGS. 4F and 6F are sectional views of reflector 320 respectively taken along line 4F-4F and 6F-6F. FIGS. 5 and 7 are optical-path diagrams illustrating optical paths of typical light beams included in ultraviolet radiation emitted from light emitting element 310.

As illustrated in FIGS. 3, 4A to 4F and 6A to 6F, reflector 320 includes housing 322 having an inner surface serving as reflective surface 326, which will be described in detail below, and housing fixation portions 323 projecting from the side surfaces of housing 322.

Reflector 320, together with substrate 330, is fixedly attached to substrate mount 340 by insertion of screws into tapped holes 323a formed in housing fixation portions 323 toward the bottom surface of housing fixation portions 323. Further, reflector 320 is fixedly attached to transparent-plate fixation lid 234 (particularly fixation outer wall portion 234a) of channel pipe 200 by insertion of screws into tapped holes 323b formed in housing fixation portions 323 toward the front of housing fixation portion 323.

In this case, it is preferable that reflector 320 be attached in such a position that the bottom surface of housing 322 is substantially coplanar with the upper surface of light emitting element 310. However, reflector 320 may also be attached such that the bottom surface of housing 322 is situated vertically above the upper surface of light emitting element 310.

When reflector 320 is attached to substrate mount 340 together with substrate 330 on which light emitting element 310 is mounted, light emitting element 310 is disposed in opening portion 325 formed in the bottom surface of reflector 320 or outside of opening portion 325, so that reflective surface 326 that is the inner surface of housing 322 is disposed to face the upper surface of light emitting element 310. Further, when reflector 320 is mounted on transparent-plate fixation lid 234, the opening portion (exit aperture 327) formed in the front of reflector 320 is disposed to face treatment channel 220 via transparent plate 250. In this case, optical axis OA of light emitting element 310 is substantially orthogonal to axis PA of treatment channel 220, and virtual axis EA set to be oriented in the direction in which the light flux of ultraviolet radiation reflected on reflective surface 326 exits from exit aperture 327 is orthogonal to optical axis OA of light emitting element 310 and parallel to axis PA of treatment channel 220. Thus, the ultraviolet radiation emitted from light emitting element 310 is reflected on and collected by reflective surface 326, exits from exit aperture 327, and is directed onto treatment channel 220 via transparent plate 250. Note that optical axis OA of the light emitting element means a light beam at the center of a three-dimensional light flux exiting light emitting element 310.

More specifically, the inner surface of housing 322 is reflective surface 326 that reflects ultraviolet radiation, reflects the ultraviolet radiation emitted from light emitting element 310 in the direction substantially orthogonal to optical axis OA of light emitting element 310, collects the ultraviolet radiation, and causes the ultraviolet radiation to travel in the direction of exit aperture 327 (which is also the direction of virtual axis EA).

Reflective surface 326 is shaped to be similar in section to a parabola (see FIGS. 1, 4F, 5, 6F and 7) and to be rotationally symmetrical with respect to one of virtual axes EA set to be oriented in the exit direction of the reflected ultraviolet radiation, in which, however, a portion of the rotationally symmetrical solid shape which does not contribute to reflection of the ultraviolet radiation emitted from light emitting element 310 is cut out. Reflective surface 326 is shaped to reflect the ultraviolet radiation emitted from light emitting element 310 and cause most of the reflected ultraviolet radiation to be an exiting light beam traveling from exit aperture 327 toward treatment channel 220 when reflective surface 326 is regarded as a parabolic surface and light emitting element 310 is disposed in position FP regarded as a focal point of reflective surface 326.

More specifically, it is preferable that reflective surface 326 be shaped to be capable of reflecting the ultraviolet radiation emitted from light emitting element 310 such that following condition 1 is satisfied, when the exit angle of one light beam included in the ultraviolet radiation exiting from the emission center of light emitting element 310 is denoted by $\theta 1$ and the exit angle of the light beam emitted at exit angle $\theta 1$, reflected on reflective surface 326, and exiting from exit aperture 327 is denoted by $\theta 2$.

Condition 1: in the ranges of $-60°<\theta 1<-5°$ and $5°<\theta 1<60°$, the absolute value of exit angle $\theta 2$ of the reflected light beam being an emitted light beam reflected on the reflected surface is less than the absolute value of exit angle $\theta 1$ of the emitted light beam.

As illustrated in FIGS. 5 and 7, $\theta 1$ is an angle (0 degrees or greater and 90 degrees or less) formed by one light beam included in the ultraviolet radiation emitted from the emission center of light emitting element 310 (hereinafter, such a light beam is simply referred to as the "emitted light beam") with optical axis OA of light emitting element 310. In the present specification, angle $\theta 1$ formed by the emitted light beam is defined as a positive value when the emitted light beam travels obliquely with respect to optical axis OA in a direction opposite to exit direction ED (the opposite direction is a direction opposite to the traveling direction of virtual axis EA, a direction opposite to the direction from light emitting element 310 toward channel pipe 200, and a direction opposite to the direction from light emitting element 310 toward exit aperture 327), and, angle $\theta 1$ of the emitted light beam is defined as a negative value when the emitted light beam travels obliquely with respect to optical axis OA in the exit direction (which is the traveling direction of virtual axis EA, the direction from light emitting element 310 toward channel pipe 200, and the direction from light emitting element 310 toward exit aperture 327).

In addition, as illustrated in FIGS. 5 and 7, $\theta 2$ is an angle (0 degrees or greater and 90 degrees or less) formed by one light beam included in the ultraviolet radiation emitted from light emitting element 310 and reflected on reflective surface 326 (hereinafter, such a light beam is simply referred to as the "reflected light beam") with virtual axis EA. In the present specification, angle $\theta 2$ formed by the reflected light beam is defined as a positive value when the reflected light beam travels obliquely with respect to axis PA of treatment channel 220 and virtual axis EA in the traveling direction of optical axis OA, and, angle $\theta 2$ formed by the reflected light beam is defined as a negative value when the reflected light beam travels obliquely with respect to axis PA of treatment channel 220 and virtual axis EA in a direction opposite to the traveling direction of optical axis OA.

Condition 1 means that, in the ranges of $-60°<\theta1<-5°$ and $5°<\theta1<60°$, exiting light beams do not spread and are collected in the direction of exit aperture 327. When condition 1 is satisfied, the light beams included in the ultraviolet radiation emitted from light emitting element 310 and reflected are mostly the exiting light beams traveling from exit aperture 327 toward treatment channel 220. Accordingly, the ultraviolet radiation exiting ultraviolet irradiation apparatus 300 having reflector 320 which satisfies condition 1 is unlikely to spread and is likely to propagate through treatment channel 220 along a shorter path in the longitudinal direction of treatment channel 220 without being reflected on channel wall 225. Thus, the illuminance of the ultraviolet radiation emitted from ultraviolet irradiation apparatus 300 is unlikely to decrease in treatment channel 220, and the ultraviolet radiation emitted from ultraviolet irradiation apparatus 300 can propagate a longer distance within treatment channel 220 while retaining a higher illuminance.

In one aspect of the present embodiment, from the viewpoint of increasing the fluid sterilization efficiency in the treatment channel, it is preferable that reflective surface 326 be shaped to be capable of reflecting the ultraviolet radiation emitted from light emitting element 310 such that following condition 2 and above-described condition 1 are satisfied.

Condition 2: in the range of $-50°<\theta1<50°$, the difference between the maximum value of $\theta2$ and the minimum value of $\theta2$ is less than $3°$.

Condition 2 means that the exiting light beam is not significantly oblique to virtual axis EA in the range of $-50°<\theta1<50°$. When condition 2 is satisfied, the ultraviolet radiation emitted from light emitting element 310 and reflected is collected and propagates while retaining a higher illuminance of the central portion of the light flux where most reflected light beams are gathered. Therefore, the ultraviolet radiation exiting ultraviolet irradiation apparatus 300 having the reflector which satisfies condition 2 is likely to propagate through treatment channel 220 even to a position distant from the exit aperture while retaining a higher illuminance of the central portion of the light flux.

Note that reflective surface 326 only have to be shaped to be able to satisfy conditions 1 and 2 when light emitting element 310 is disposed in aforementioned position FP regarded as the focal point.

In another aspect of the present embodiment, from the viewpoint of increasing the fluid sterilization efficiency in the treatment channel, it is preferable that reflective surface 326 be shaped to be capable of reflecting the ultraviolet radiation emitted from light emitting element 310 such that following condition 3 and above-described condition 1 are satisfied.

Condition 3: in the range of $-40°<\theta1<55°$, $\theta2$ increases as $\theta1$ decreases.

Condition 3 means that exiting light beams spread without overlapping each other in the range of $-40°<\theta1<55°$. When condition 3 is satisfied, the ultraviolet radiation emitted from light emitting element 310 and reflected is unlikely to be gathered at the central portion of the light flux so as not to become spot-like, and is likely to propagate while retaining a more uniform illuminance distribution.

Note that reflective surface 326 only have to be shaped to be able to satisfy conditions 1 and 3 when light emitting element 310 is disposed in aforementioned position FP regarded as the focal point.

In either of the above-described aspects, it is preferable that ultraviolet irradiation apparatus 300 be disposed such that the central portion of the light flux at which the brightness of the ultraviolet radiation exiting from exit aperture 327 is the highest is disposed more closely to axis PA of treatment channel 220, and it is more preferable that the aforementioned central portion of the light flux be disposed in substantial alignment with axis PA of treatment channel 220. Note that, of the ultraviolet radiation exiting ultraviolet irradiation apparatus 300, the central portion of the light flux exiting from exit aperture 327 is slightly offset in the traveling direction of optical axis OA from the position of the light emitting surface of light emitting element 310 as disposed, and therefore, it is preferable that light emitting element 310 be disposed such that the position of the light emitting surface is offset from axis PA of treatment channel 220 in a direction opposite to the traveling direction of optical axis OA.

Ultraviolet irradiation apparatus 300 is formed, for example, of a metal material, a glass, a resin material, and the like. However, it is preferable that reflective surface 326 be formed of a material with high UV reflectivity. For example, it is preferable that reflective surface 326 be formed of: mirror-polished aluminum (Al); an aluminum film disposed on the surface of glass, a resin material, or the like; polytetrafluoroethylene (PTFE); or the like. The method of making the aluminum film is not particularly limited and the aluminum film may be made, for example, by vacuum deposition or the like.

In addition, from the viewpoint of controlling traveling of light beams in the channel pipe, it is preferable that reflective surface 326 be a surface that reflects ultraviolet radiation specularly rather than diffusely.

Figure 8A:
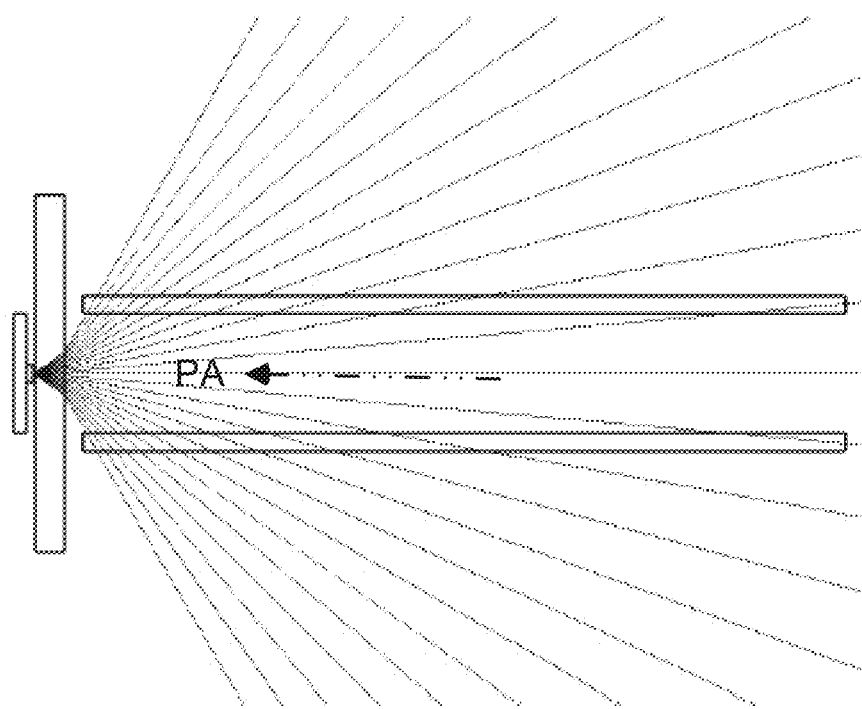
FIG. 8A illustrates an exemplary optical-path diagram for a case where ultraviolet radiation emitted from a light emitting element disposed to face a treatment channel is directed onto a treatment channel via a transparent plate without use of any reflector.

FIG. 8A illustrates an exemplary optical-path diagram for a case where the ultraviolet radiation emitted from the light emitting element disposed to face the treatment channel is directed onto the treatment channel via the transparent plate without use of the reflector. The emitted ultraviolet radiation is directed onto the treatment channel while spreading at a wide angle. In this case, when the channel wall of the treatment channel is formed of a material with high UV reflectivity, the ultraviolet radiation directed onto the treatment channel propagates through the treatment channel while reflected on the channel wall. However, when much of the ultraviolet radiation is reflected on the channel wall, it is difficult to control the illuminance distribution in the treatment channel, and it is difficult to increase the illuminance near axis PA, which is the center of the treatment channel. Moreover, when much of the ultraviolet radiation is reflected on the channel wall, each light beam included in the ultraviolet radiation propagates through treatment channel 220 along a longer path in the longitudinal direction of treatment channel 220, so that the illuminance is likely to decrease as the light beam travels longer distance through treatment channel 220 in the longitudinal direction.

Figure 8B:
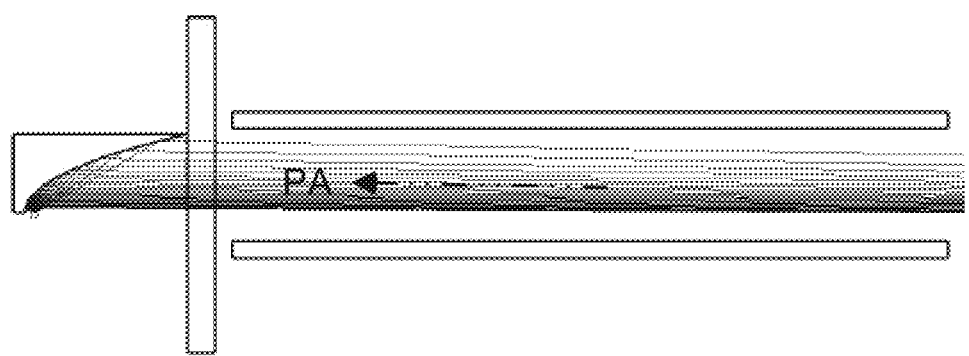
FIG. 8B illustrates an exemplary optical-path diagram for a case where an ultraviolet irradiation apparatus including a reflector according to one aspect of an embodiment of the present invention is used, and the ultraviolet radiation emitted from the light emitting element is directed onto the treatment channel via the transparent plate.

FIG. 8B illustrates an exemplary optical-path diagram for a case where ultraviolet irradiation apparatus 300 including reflector 320 which satisfies conditions 1 and 2 according to the above-described one aspect of the present embodiment is used, and the ultraviolet radiation emitted from light emitting element 310 is directed onto the treatment channel via the transparent plate. In addition, the ultraviolet radiation passing through transparent plate 250 propagates through the treatment channel while retaining a higher illuminance near axis PA, which is the center of the treatment channel.

Figure 8C:
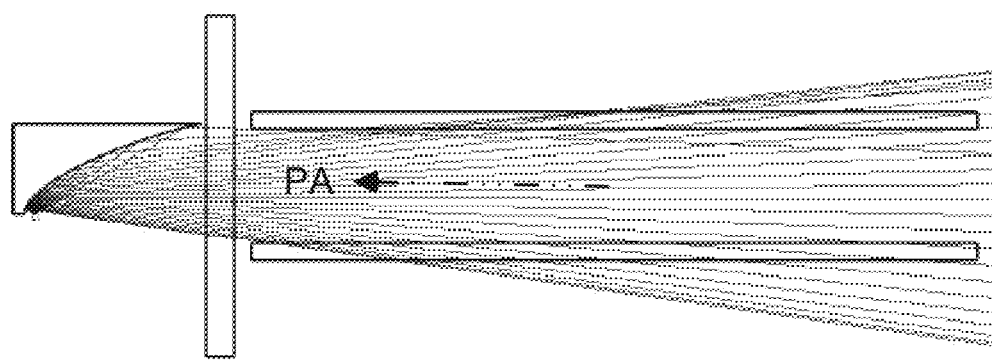
FIG. 8C illustrates an exemplary optical-path diagram for a case where an ultraviolet irradiation apparatus including a reflector according to another aspect of an embodiment of the present invention is used, and the ultraviolet radiation emitted from the light emitting element is directed onto the treatment channel via the transparent plate.

FIG. 8C illustrates an exemplary optical-path diagram for a case where ultraviolet irradiation apparatus 300 including reflector 320 which satisfies conditions 1 and 3 according to the above-described other aspect of the present embodiment is used, and the ultraviolet radiation emitted from light emitting element 310 is directed onto the treatment channel via the transparent plate. In addition, the ultraviolet radiation passing through transparent plate 250 propagates through treatment channel 220 while uniformly spreading within treatment channel 220.

As is understood, when ultraviolet irradiation apparatus 300 according to the present embodiment is used, the illuminance distribution in the treatment channel is easily controlled. In addition, when ultraviolet irradiation apparatus 300 according to the above-described one aspect is used, each light beam included in the ultraviolet radiation propagates through treatment channel 220 along a shorter path in the longitudinal direction of treatment channel 220, so that the light beam can propagate a longer distance in the longitudinal distance in treatment channel 220 while retaining high illuminance.

Further, according to the present embodiment, the ultraviolet radiation emitted from light emitting element 310 is collected by reflector 320 and directed onto treatment channel 220. It is thus easy in the present embodiment to control the optical path of the ultraviolet radiation emitted from light emitting element 310 so as to adjust the illuminance distribution of the ultraviolet radiation in treatment channel 220.

Further, according to the present embodiment, the emitted ultraviolet radiation is collected by reflector 320 whose reflective surface 326 satisfies condition 1, so that the illuminance of the ultraviolet radiation in treatment channel 220 is unlikely to decrease, and the ultraviolet radiation can propagate a long distance in treatment channel 220 in the longitudinal direction.

Further, according to the above-described one aspect of the present embodiment, the emitted ultraviolet radiation is collected by reflector 320 whose reflective surface 326 satisfies condition 2, so that the exiting ultraviolet radiation is likely to propagate through treatment channel 220 even to a position distant from the exit aperture while retaining a higher illuminance near axis PA, which is the center of the treatment channel.

In addition, according to the above-described other aspect of the present embodiment, the emitted ultraviolet radiation is collected by reflector 320 whose reflective surface 326 satisfies condition 3, the emitted ultraviolet radiation is unlikely to be gathered at the central portion of the light flux so as not to become spot-like, and is likely to propagate while retaining a more uniform illuminance distribution.

As is understood, in the present embodiment, it is possible to enhance the sterilization effect over the entire treatment channel by causing the light of ultraviolet radiation exiting the light emitting element to be reflected on the reflective surface that collects the light toward the channel pipe so as to control the light flux of the ultraviolet radiation.

[Simulation Result of Illuminance Distribution]

Hereinafter, a description will be given of simulation results of illuminance distribution of ultraviolet radiation in treatment channel 220 for a case where the ultraviolet radiation is directed onto treatment channel 220 using ultraviolet sterilization apparatus 100 including ultraviolet irradiation apparatus 300. For comparison, a description will also be given of simulation results of illuminance distribution of ultraviolet radiation in the treatment channel for a case (see FIG. 8A) where the ultraviolet radiation emitted from the light emitting element disposed to face the treatment channel is directed onto the treatment channel using an ultraviolet sterilization apparatus not including ultraviolet irradiation apparatus 300.

The simulations were conducted under the following setting conditions.

(Setting Conditions 1 and 2)

Ultraviolet irradiation apparatus 300 as illustrated in FIG. 1 was provided by attaching, to substrate mount 340, a substrate on which light emitting element 310 being an LED is mounted, and reflector 320 having reflective surface 326 which satisfies conditions 1 and 2 (Example 1) or conditions 1 and 3 (Example 2). Note that light emitting element 310 was disposed in position FP that is to serve as the focal point when reflective surface 326 of reflector 320 is regarded as a parabolic surface. Note also that, reflector 320 was attached such that its bottom surface is coplanar with the upper surface of light emitting element 310. Ultraviolet irradiation apparatus 300 was fixedly attached to channel pipe 200 whose channel wall 225 reflects ultraviolet radiation and which has treatment channel 220. At this time, ultraviolet irradiation apparatus 300 was disposed such that the upper surface of light emitting element 310 is slightly vertically below axis PA of treatment channel 220.

Light emitting element 310, reflector 320, transparent plate 250, and treatment channel 220, as well as their positional relationship were set as follows.

The center wavelength of the light emitting element: 265 nm

The beam angle of full width at half maximum of the light emitting element: 105°

The outer diameter of the exit surface of the light emitting element: φ3 mm (the chip size is 1 mm×1 mm)

The distance between the optical axis of the light emitting element and the transparent plate: 30.4 mm The shape of the exit aperture of the reflector: semicircular The inner diameter of the exit aperture of the reflector: φ32 mm The thickness of the transparent plate: 2 mm The cross-sectional shape of the treatment channel: circular The inner diameter of the treatment channel: 20 mm The length of the treatment channel: 140 mm The fluid in the treatment channel: water ($H_2O$)

Table 1 shows the relationship between angle θ1 formed by an emitted light beam with optical axis OA of light emitting element 310 and angle θ2 formed by a reflected light beam with virtual axis EA in Example 1, and Table 2 shows the relationship between said angle θ1 and said angle θ2 in Example 2 in this ultraviolet irradiation apparatus.

TABLE 1

| θ1(°) | θ2(°) |
|---|---|
| 60 | −0.3 |
| 55 | −0.3 |
| 50 | −0.4 |
| 45 | −0.4 |
| 40 | −0.4 |
| 35 | −0.4 |
| 30 | −0.4 |
| 25 | −0.4 |
| 20 | −0.4 |
| 15 | −0.4 |
| 10 | −0.5 |
| 5 | −0.5 |
| 0 | −0.5 |
| −5 | −0.5 |

TABLE 1-continued

| θ1(°) | θ2(°) |
|---|---|
| −10 | −0.5 |
| −15 | −0.6 |
| −20 | −0.6 |
| −25 | −0.6 |
| −30 | −0.7 |
| −35 | −0.7 |
| −40 | −0.7 |
| −45 | −0.8 |
| −50 | −0.8 |
| −55 | −0.9 |
| −60 | −1.0 |

TABLE 2

| θ1(°) | θ2(°) |
|---|---|
| 60 | −8.1 |
| 55 | −8.0 |
| 50 | −7.6 |
| 45 | −7.1 |
| 40 | −6.4 |
| 35 | −5.6 |
| 30 | −4.7 |
| 25 | −3.8 |
| 20 | −2.8 |
| 15 | −1.9 |
| 10 | −1.0 |
| 5 | −0.2 |
| 0 | 0.7 |
| −5 | 1.5 |
| −10 | 2.2 |
| −15 | 2.9 |
| −20 | 3.6 |
| −25 | 4.4 |
| −30 | 5.1 |
| −35 | 5.7 |
| −40 | 6.1 |
| −45 | 5.8 |
| −50 | 4.6 |
| −55 | 3.6 |
| −60 | −1.8 |

(Setting Condition 3)

For comparison, the same light emitting element was disposed to face the treatment channel such that axis PA of the treatment channel and optical axis OA of the light emitting element coincide with each other. The distance between the exit surface of the light emitting element and the transparent plate was 0.1 mm. In other respects, condition 3 was set the same as setting conditions 1 and 2.

(Simulation 1)

Under each of setting conditions 1 and 3, the distribution of illuminances on axis PA of the treatment channel (hereinafter, such illuminance is also simply referred to as "center illuminance") in the longitudinal direction of the treatment channel (7.5 mm to 135.5 mm from the transparent plate) and the distribution of the minimum value among illuminances at the upper end, lower end, right end, and left end of the treatment channel (hereinafter, such illuminance is also simply referred to as "peripheral illuminance") were examined.

Figure 9A:
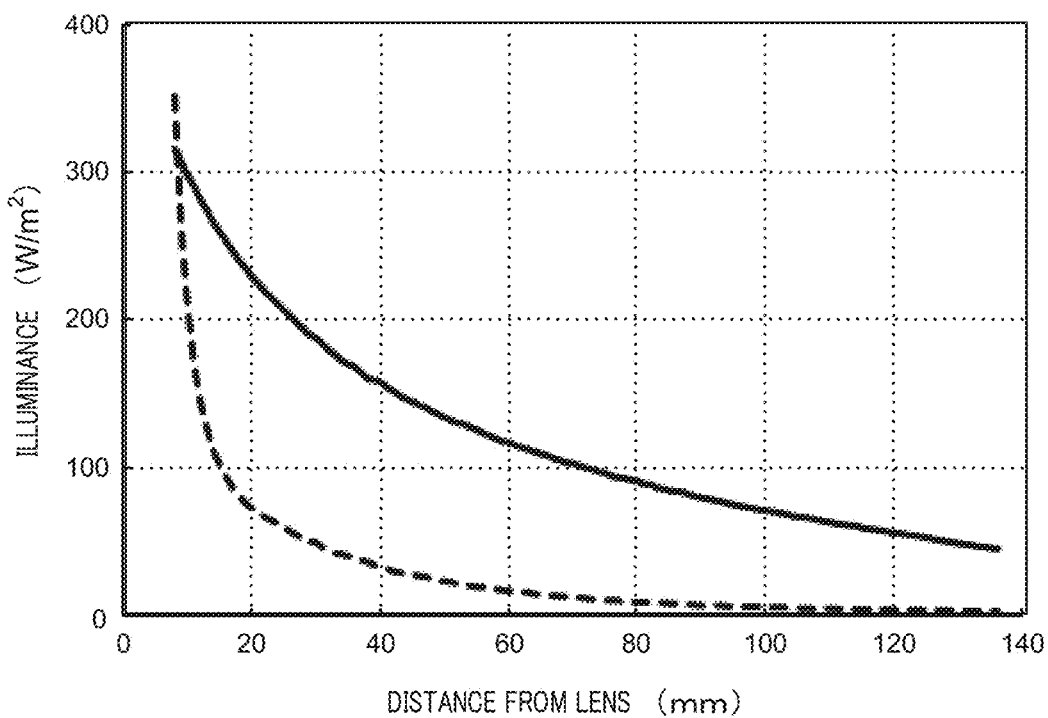
FIG. 9A is a graph that is obtained from a simulation of illuminance distribution under setting conditions 1 and 3 described herein and by plotting the distance from the transparent plate on the X-axis and the illuminance at the distance on the Y-axis, and that illustrates a distribution of center illuminances under setting conditions 1 and 3.

FIG. 9A is a graph that is obtained by plotting the distance from the transparent plate on the X-axis and the illuminance at the distance on the Y-axis, and illustrates the distributions of center illuminances under setting conditions 1 and 3. In FIG. 9A, the solid line illustrates the simulation result under setting condition 1, and the dashed line illustrates the simulation result under setting condition 3. Under setting condition 1 in which ultraviolet irradiation apparatus 300 is used, the ultraviolet radiation propagated through the treatment channel while retaining a high center illuminance to a position more distant from the transparent plate than under setting condition 3 in which ultraviolet irradiation apparatus 300 is not used.

Figure 9B:
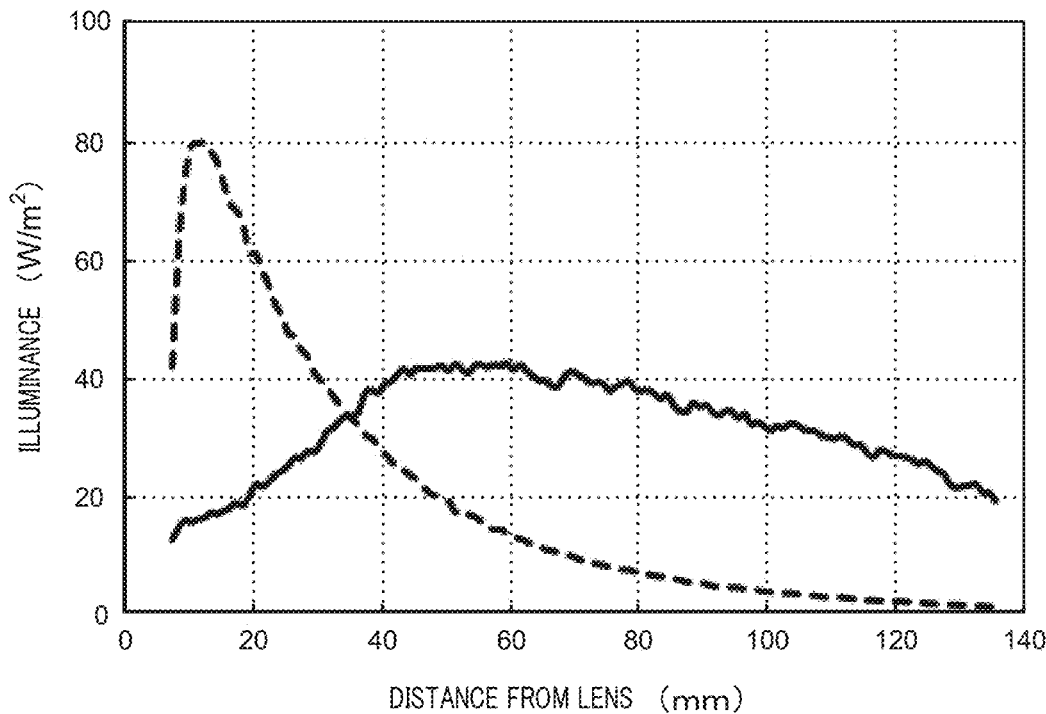
FIG. 9B is a graph that is obtained from a simulation of illuminance distribution under setting conditions 1 and 3 described herein and by plotting the distance from the transparent plate on the X-axis and the illuminance at the distance on the Y-axis, and that illustrates a distribution of peripheral illuminances under setting conditions 1 and 3.

FIG. 9B is a graph that is obtained by plotting the distance from the transparent plate on the X-axis and the illuminance at the distance on the Y-axis, and illustrates the distributions of peripheral illuminances under setting conditions 1 and 3. In FIG. 9B, the solid line illustrates the simulation result under setting condition 1, and the dashed line illustrates the simulation result under setting condition 3. Under setting condition 1 in which ultraviolet irradiation apparatus 300 is used, the ultraviolet radiation propagated through the treatment channel while retaining a high peripheral illuminance to a position more distant from the transparent plate than under setting condition 3 in which ultraviolet irradiation apparatus 300 is not used.

These results shows that, under setting condition 1 in which ultraviolet irradiation apparatus 300 is used, the ultraviolet radiation propagates through the treatment channel while retaining a higher illuminance over the entire region of the treatment channel in the sectional direction than under setting condition 3 in which ultraviolet irradiation apparatus 300 is not used.

(Simulation 2)

Under each of setting conditions 1 and 3, the illuminance distribution on the horizontal line passing axis PA of the treatment channel at the position 8 mm from the transparent plate and the illuminance distribution on the horizontal line passing axis PA of the treatment channel at the position 72 mm from the transparent plate were examined.

Figure 10A:
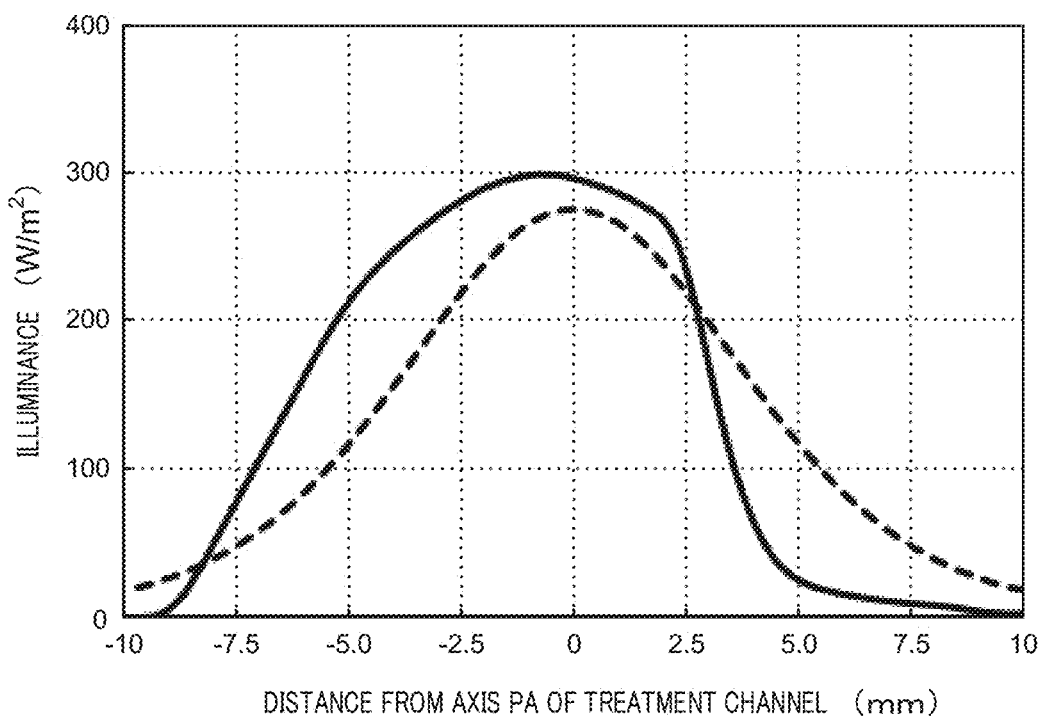
FIG. 10A is a graph that is obtained from a simulation of illuminance distribution under setting conditions 1 and 3 described herein and by plotting on the X-axis the distance from axis PA of the treatment channel at a position 8 mm distant from the transparent plate and plotting on the Y-axis the illuminance at the distance, and that illustrates a distribution of illuminances under setting conditions 1 and 3.

FIG. 10A is a graph that is obtained by plotting on the X-axis the distance from axis PA of the treatment channel at the position 8 mm from the transparent plate and plotting on the Y-axis the illuminance at the distance, and that illustrates the distributions of illuminances under setting conditions 1 and 3. In FIG. 10A, the solid line illustrates the simulation result under setting condition 1, and the dashed line illustrates the simulation result under setting condition 3.

Figure 10B:
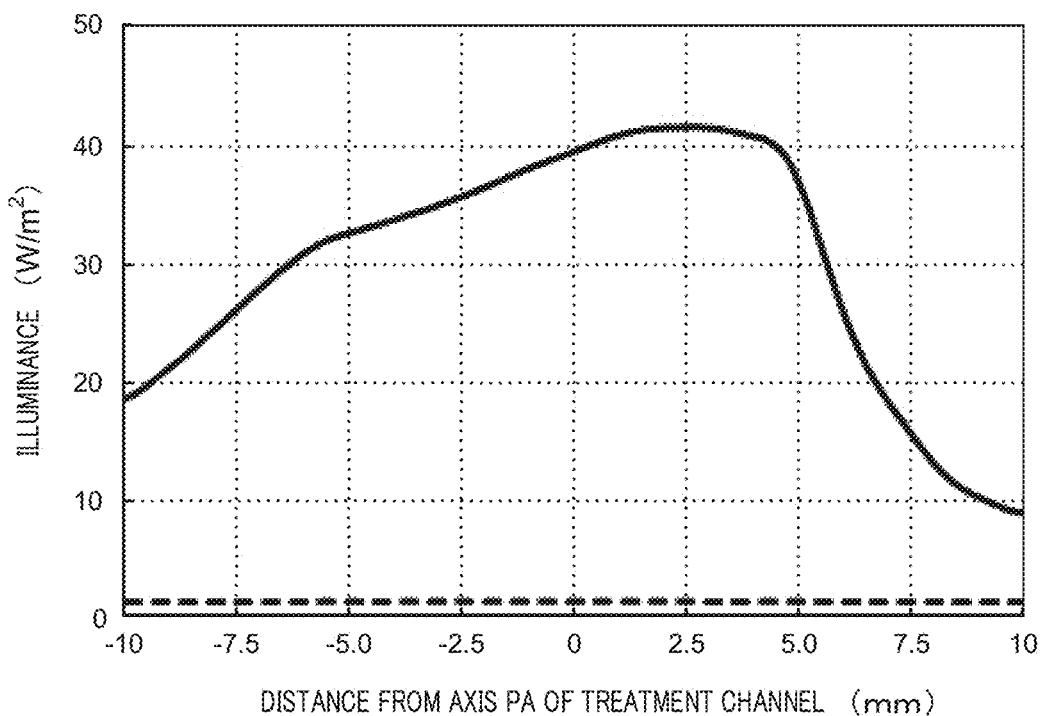
FIG. 10B is a graph that is obtained from a simulation of illuminance distribution under setting conditions 1 and 3 described herein and by plotting on the X-axis the distance from axis PA of the treatment channel at a position 72 mm distant from the transparent plate and plotting on the Y-axis the illuminance at the distance, and that illustrates a distribution of illuminances under setting conditions 1 and 3.

FIG. 10B is a graph that is obtained by plotting on the X-axis the distance from axis PA of the treatment channel at the position 72 mm from the transparent plate and plotting on the Y-axis the illuminance at the distance, and that illustrates the distributions of illuminances under setting conditions 1 and 3. In FIG. 10B, the solid line illustrates the simulation result under setting condition 1, and the dashed line illustrates the simulation result under setting condition 3.

Under setting condition 1 in which ultraviolet irradiation apparatus 300 is used, peaks of the illuminance distribution were formed near axis PA of the treatment channel in both cases of the position 8 mm from the transparent plate and the position 72 mm from the transparent plate. In contrast, under setting condition 3 in which ultraviolet irradiation apparatus 300 is not used, a peak of the illuminance distribution was formed near axis PA of the treatment channel in the case of the position 8 mm from the transparent plate, but a peak of the illuminance distribution was not formed near axis PA of the treatment channel in the case of the position 72 mm from the transparent plate.

These results shows that, under setting condition 1 in which ultraviolet irradiation apparatus 300 is used, the ultraviolet radiation propagates a longer distance in the longitudinal direction of treatment channel 220 while retaining a higher center illuminance than under setting condition 3 in which ultraviolet irradiation apparatus 300 is not used.

(Simulation 3)

A simulation the same as aforementioned simulation 1 but with setting condition 1 being changed to setting condition 2 was conducted.

Figure 11A:
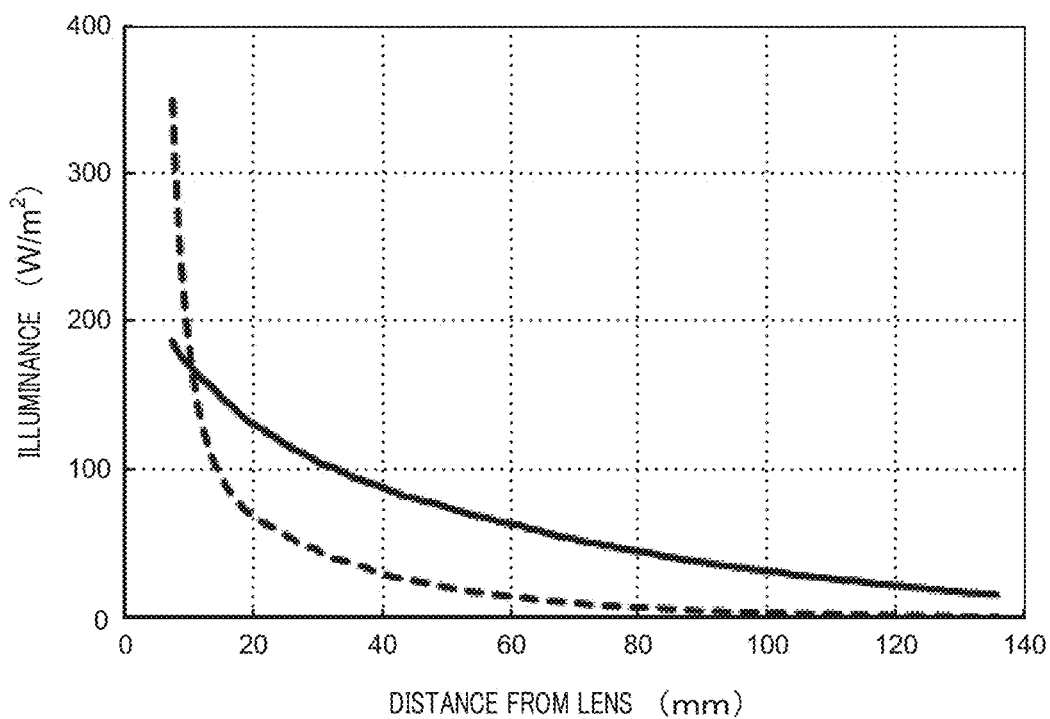
FIG. 11A is a graph that is obtained from a simulation of illuminance distribution under setting conditions 2 and 3 described herein and by plotting the distance from the transparent plate on the X-axis and the illuminance at the distance on the Y-axis, and that illustrates a distribution of center illuminances under setting conditions 2 and 3.

FIG. 11A is a graph that is obtained by plotting the distance from the transparent plate on the X-axis and the illuminance at the distance on the Y-axis, and that illustrates the distributions of center illuminances under setting conditions 2 and 3. In FIG. 11A, the solid line illustrates the simulation result under setting condition 2, and the dashed line illustrates the simulation result under setting condition 3. Under setting condition 2 in which ultraviolet irradiation apparatus 300 is used, the ultraviolet radiation propagated through the treatment channel while retaining a high center illuminance to a position more distant from the transparent plate than under setting condition 3 in which ultraviolet irradiation apparatus 300 is not used.

Figure 11B:
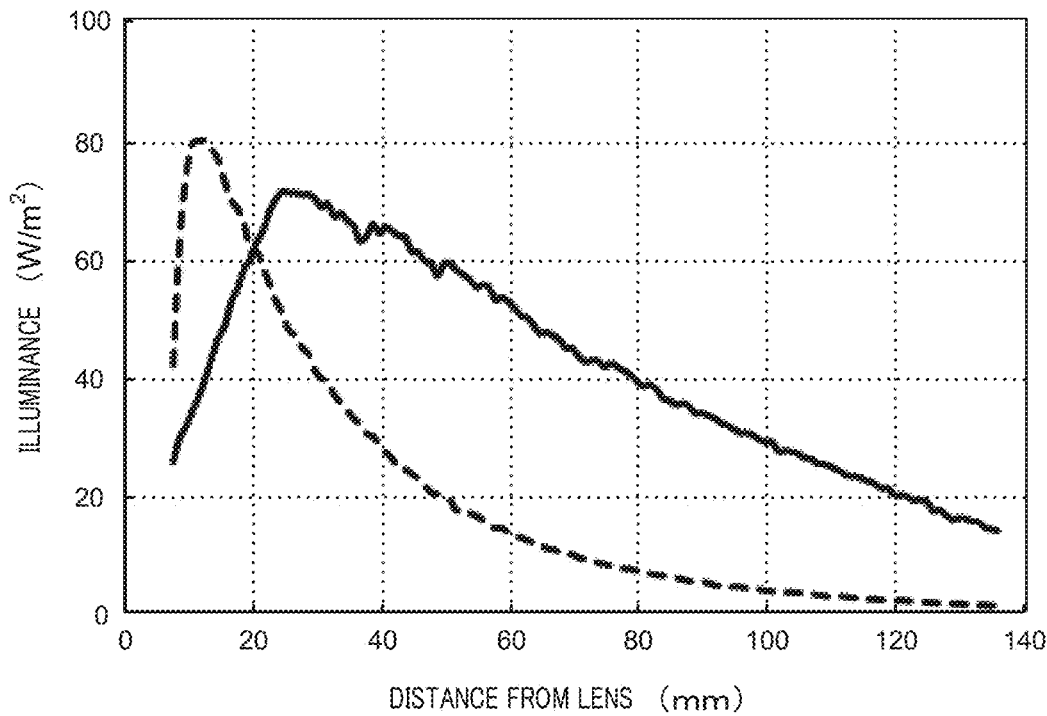
FIG. 11B is a graph that is obtained from a simulation of illuminance distribution under setting conditions 2 and 3 described herein and by plotting the distance from the transparent plate on the X-axis and the illuminance at the distance on the Y-axis, and that illustrates a distribution of peripheral illuminances under setting conditions 2 and 3.

FIG. 11B is a graph that is obtained by plotting the distance from the transparent plate on the X-axis and the illuminance at the distance on the Y-axis, and that illustrates the distributions of peripheral illuminances under setting conditions 2 and 3. In FIG. 11B, the solid line illustrates the simulation result under setting condition 2, and the dashed line illustrates the simulation result under setting condition 3. Under setting condition 2 in which ultraviolet irradiation apparatus 300 is used, the ultraviolet radiation propagated through the treatment channel while retaining a high peripheral illuminance to a position more distant from the transparent plate than under setting condition 3 in which ultraviolet irradiation apparatus 300 is not used.

These results shows that, under setting condition 2 in which ultraviolet irradiation apparatus 300 is used, the ultraviolet radiation propagates a longer distance in the longitudinal direction of treatment channel 220 while retaining a higher illuminance over the entire region of the treatment channel in the sectional direction than under setting condition 3 in which ultraviolet irradiation apparatus 300 is not used.

(Simulation 4)

A simulation the same as aforementioned simulation 2 but with setting condition 1 being changed to setting condition 2 was conducted.

Figure 12A:
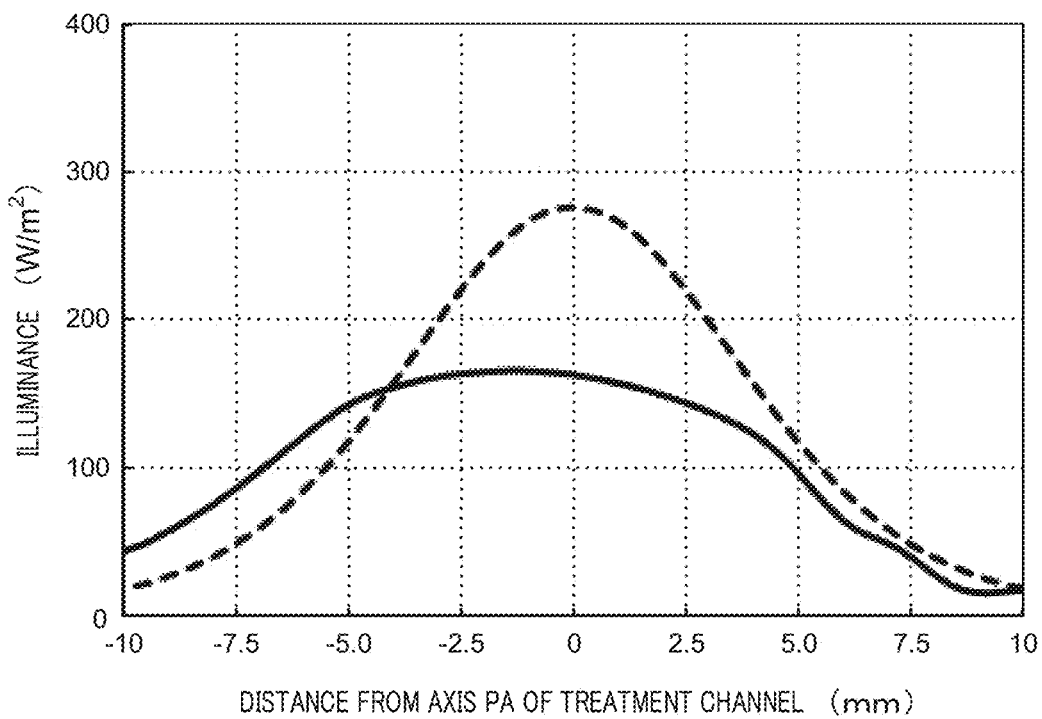
FIG. 12A is a graph that is obtained from a simulation of illuminance distribution under setting conditions 2 and 3 described herein and by plotting on the X-axis the distance from axis PA of the treatment channel at a position 8 mm distant from the transparent plate and plotting on the Y-axis the illuminance at the distance, and that illustrates a distribution of illuminances under setting conditions 2 and 3.

FIG. 12A is a graph that is obtained by plotting on the X-axis the distance from axis PA of the treatment channel at the position 8 mm from the transparent plate and plotting on the Y-axis the illuminance at the distance, and that illustrates the distributions of illuminances under setting conditions 2 and 3. In FIG. 12A, the solid line illustrates the simulation result under setting condition 2, and the dashed line illustrates the simulation result under setting condition 3.

Figure 12B:
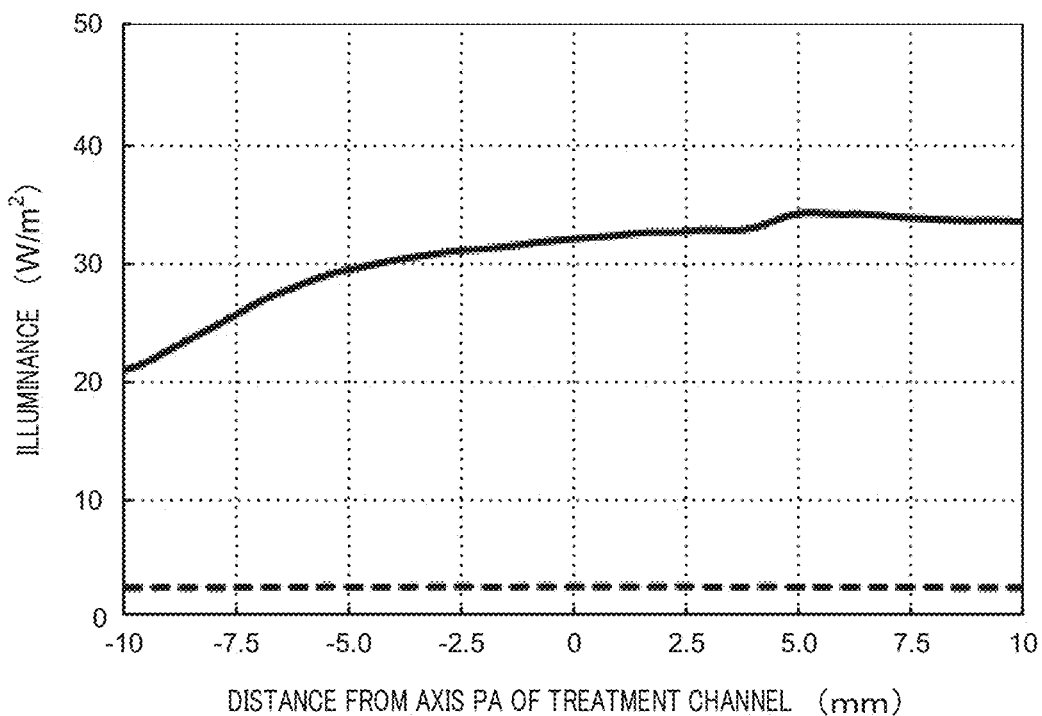
FIG. 12B is a graph that is obtained from a simulation of illuminance distribution under setting conditions 2 and 3 described herein and by plotting on the X-axis the distance from axis PA of the treatment channel at a position 72 mm distant from the transparent plate and plotting on the Y-axis the illuminance at the distance, and that illustrates a distribution of illuminances under setting conditions 2 and 3.

FIG. 12B is a graph that is obtained by plotting on the X-axis the distance from axis PA of the treatment channel at the position 72 mm from the transparent plate and plotting on the Y-axis the illuminance at the distance, and that illustrates the distributions of illuminances under setting conditions 2 and 3. In FIG. 12B, the solid line illustrates the simulation result under setting condition 2, and the dashed line illustrates the simulation result under setting condition 3.

The difference between the center illuminance and the peripheral illuminance at the position 8 mm from the transparent plate was smaller under setting condition 2 in which ultraviolet irradiation apparatus 300 is used than under setting condition 3 in which ultraviolet irradiation apparatus 300 is not used. Under setting condition 2 in which ultraviolet irradiation apparatus 300 is used, the ultraviolet radiation propagated with the difference between the center illuminance and the peripheral illuminance remaining small even at the position 72 mm from the transparent plate.

These results shows that, under setting condition 2 in which ultraviolet irradiation apparatus 300 is used, the ultraviolet radiation propagates through the treatment channel by a longer distance in the longitudinal direction of the treatment channel while retaining a more uniform illuminance distribution in the sectional direction than under setting condition 3 in which ultraviolet irradiation apparatus 300 is not used.

Other Embodiments

Note that, the above-described embodiment merely describes an example of implementations for practicing an invention, and should not be construed as limiting the technical scope of the present invention. That is, the present invention can be embodied in various forms without departing from the spirit, scope, or principal features of the present invention.

For example, although the ultraviolet irradiation apparatus is disposed such that ultraviolet radiation is directed in a direction opposite to the flowing direction of the fluid flowing through the treatment channel in the above-described embodiment, the ultraviolet irradiation apparatus may also be disposed such that ultraviolet radiation is directed in a forward direction along the flowing direction of the fluid.

In addition, in order to more uniformly sterilize the inside of the treatment channel entirely with a more uniform illuminance distribution, the ultraviolet radiation may be directed onto the treatment channel while the ultraviolet irradiation apparatus is rotated.

The present application claims the benefit of priority based on Japanese Patent Application No. 2017-188148 filed on Sep. 28, 2017, the disclosure of which including the specification, claims, and drawings is incorporated herein by reference in its entirety.

INDUSTRIAL APPLICABILITY

According to the present invention, it is possible to enhance the sterilization effect of an ultraviolet sterilization apparatus for sterilizing a fluid flowing through a treatment channel. Accordingly, the spread of ultraviolet sterilization apparatuses for sterilizing service water, agricultural fluids, and/or the like, and further development of this technical field are expected from the present invention.

REFERENCE SIGNS LIST

100 Ultraviolet sterilization apparatus
200 Channel pipe
210 Inflow port
212 Fit-in portion
216 Inflow engagement portion
220 Treatment channel
225 Channel wall
230 End portion
232 Transparent-plate holding portion
232$a$ End-portion outer wall portion
232$b$ Transparent-plate disposing portion
232$c$ Flow-rate attenuation portion
234 Transparent-plate fixation lid
234$a$ Fixation outer wall portion
234$b$ Ultraviolet irradiation hole
240 Outflow port 244 Opening
245 Outflow channel
246 Outflow engagement portion
250 Transparent plate
300 Ultraviolet irradiation apparatus
310 Light emitting element
320 Reflector
322 Housing
323 Housing fixation portion
323a, 323b Tapped hole
325 Opening portion
326 Reflective surface
327 Exit aperture
330 Substrate
340 Substrate mount

What is claimed is:

1. An ultraviolet sterilization apparatus that sterilizes a fluid flowing through a linear treatment channel by irradiation of the fluid with ultraviolet radiation, the ultraviolet sterilization apparatus, comprising:
    a channel pipe having therein the linear treatment channel;
    a light emitting element that emits the ultraviolet radiation and that has an optical axis; and
    a reflector having a reflective surface that reflects the ultraviolet radiation emitted from the light emitting element to collect the ultraviolet radiation toward the channel pipe, wherein
    a portion of the reflector is disposed in such a position that the reflective surface faces a light emitting surface of the light emitting element, and
    the reflective surface of the reflector which includes a section at which the optical axis of the light emitting element intersects, that portion is shaped to reflect the ultraviolet radiation emitted from the light emitting element such that the following condition 1 on an exit angle $\theta 1$ of an emitted light beam emitted from an emission center of the light emitting element and an exit angle $\theta 2$ of a reflected light beam that is the emitted light beam reflected on the reflective surface is satisfied:
    Condition 1: in ranges of $-60°<\theta 1<-5°$ and $5°<\theta 1<60°$, an absolute value of the exit angle $\theta 2$ of the reflected light beam that is the emitted light beam reflected on the reflective surface is less than an absolute value of the exit angle $\theta 1$ of the emitted light beam, wherein
    an angle formed by one emitted light beam with the optical axis of the light emitting element is denoted by $\theta 1$, the one emitted light beam being included in ultraviolet radiation emitted from the emission center of the light emitting element, wherein the angle $\theta 1$ formed by the one emitted light beam is defined as a positive value when the one emitted light beam travels obliquely with respect to the optical axis in a direction opposite to a direction toward the channel pipe, and, the angle $\theta 1$ formed by the one emitted light beam is defined as a negative value when the one emitted light beam travels obliquely with respect to the optical axis in the direction toward the channel pipe, and
    an angle formed by one reflected light beam with an axis of the linear treatment channel is denoted by $\theta 2$, the one reflected light beam being included in ultraviolet radiation reflected on the reflective surface of the reflector, wherein the angle $\theta 2$ formed by the one reflected light beam is defined as a positive value when the one reflected light beam travels obliquely with respect to the axis of the linear treatment channel in a traveling direction of the optical axis, and, the angle $\theta 2$ formed by the one reflected light beam is defined as a negative value when the one reflected light beam travels obliquely with respect to the axis of the linear treatment channel in a direction opposite to the traveling direction of the optical axis.

2. The ultraviolet sterilization apparatus according to claim 1, wherein
    the reflective surface of the reflector is shaped to reflect the ultraviolet radiation emitted from the light emitting element such that the following condition 2 on the exit angle $\theta 1$ and the exit angle $\theta 2$ is further satisfied:
    Condition 2: in a range of $-50°<\theta 1<50°$, a difference between a maximum value of $\theta 2$ and a minimum value of $\theta 2$ is less than $3°$.

3. The ultraviolet sterilization apparatus according to claim 1, wherein
    the reflective surface of the reflector is shaped to reflect the ultraviolet radiation emitted from the light emitting element such that the following condition 3 on the exit angle $\theta 1$ and the exit angle $\theta 2$ is further satisfied:
    Condition 3: in a range of $-40°<\theta 1<55°$, $\theta 2$ increases as $\theta 1$ decreases.

4. The ultraviolet sterilization apparatus according to claim 1, wherein
    the light emitting element is disposed in such a direction that the ultraviolet radiation is emitted in a direction substantially orthogonal to an axis of the linear treatment channel.

5. The ultraviolet sterilization apparatus according to claim 1, wherein
    the light emitting element is disposed such that the position of a light emitting surface is offset from an axis of the linear treatment channel in a direction opposite to a traveling direction of the light from the light emitting element toward the reflections surface.

6. The ultraviolet sterilization apparatus according to claim 1, wherein
    the light emitting element and the reflector are disposed outside of the linear treatment channel.

7. The ultraviolet sterilization apparatus according to claim 6, wherein
    the channel pipe has a transparent plate at an end portion of the linear treatment channel, the transparent plate being capable of transmitting ultraviolet radiation, and
    the reflector is disposed in such a position that the ultraviolet radiation collected is directed onto the linear treatment channel via the transparent plate.

8. The ultraviolet sterilization apparatus according to claim 1, wherein
    the reflector is disposed on one end side of the linear treatment channel and in such a position that the reflective surface faces a light emitting surface of the light emitting element, and
    the fluid flowing through the linear treatment channel flows from another end side of the linear treatment channel to the one end side.

9. An ultraviolet irradiation apparatus for sterilizing a fluid flowing through a linear treatment channel by irradiation of the fluid with ultraviolet radiation, the ultraviolet irradiation apparatus, comprising:
    a light emitting element that emits the ultraviolet radiation and that has an optical axis; and
    a reflector having a reflective surface that reflects the ultraviolet radiation emitted from the light emitting element to collect the ultraviolet radiation toward a channel pipe when the channel pipe is disposed, wherein a portion of the reflector is disposed in such a position that the reflective surface faces a light emitting surface of the light emitting element, and the reflective surface of the reflector which includes a section at which the optical axis of the light emitting element intersects, that portion is shaped to reflect the ultraviolet radiation emitted from the light emitting element such that the following condition 1 on an exit angle $\theta1$ of an emitted light beam emitted from an emission center of the light emitting element and an exit angle $\theta2$ of a reflected light beam that is the emitted light beam reflected on the reflective surface is satisfied:

Condition 1: in ranges of $-60°<\theta1<-5°$ and $5°<\theta1<60°$, an absolute value of the exit angle $\theta2$ of the reflected light beam that is the emitted light beam reflected on the reflective surface is less than an absolute value of the exit angle $\theta1$ of the emitted light beam, wherein an angle formed by one emitted light beam with the optical axis of the light emitting element is denoted by $\theta1$, the one emitted light beam being included in ultraviolet radiation emitted from the emission center of the light emitting element, wherein the angle $\theta1$ formed by the one emitted light beam is defined as a positive value when the one emitted light beam travels obliquely with respect to the optical axis in a direction opposite to a direction toward the channel pipe, and, the angle $\theta1$ formed by the one emitted light beam is defined as a negative value when the one emitted light beam travels obliquely with respect to the optical axis in the direction toward the channel pipe, and an angle formed by one reflected light beam with an axis of the linear treatment channel is denoted by $\theta2$, the one reflected light beam being included in ultraviolet radiation reflected on the reflective surface of the reflector, wherein the angle $\theta2$ formed by the one reflected light beam is defined as a positive value when the one reflected light beam travels obliquely with respect to the axis of the linear treatment channel in a traveling direction of the optical axis, and, the angle $\theta2$ formed by the one reflected light beam is defined as a negative value when the one reflected light beam travels obliquely with respect to the axis of the linear treatment channel in a direction opposite to the traveling direction of the optical axis.

* * * * *